United States Patent

Hayashi et al.

[11] 4,034,003
[45] July 5, 1977

[54] 15-CYCLOALKYL-PROSTAGLANDINS

[75] Inventors: Masaki Hayashi; Seiji Kori, both of Takatsuki; Hajimu Miyake, Suita; Takashi Yamato, Takatsuki; Hisashi Suga, Nishinomiya, all of Japan

[73] Assignee: Ono Pharmaceutical Co., Ltd., Osaka, Japan

[22] Filed: Apr. 8, 1975

[21] Appl. No.: 566,147

[30] Foreign Application Priority Data

Apr. 11, 1974 United Kingdom ............ 16241/74
Nov. 8, 1974 United Kingdom ............ 48535/74

[52] U.S. Cl. .................. 260/514 D; 260/240 R; 260/343.3 R; 260/345.7; 260/345.8; 260/346.2 R; 260/468 D; 424/305; 424/317

[51] Int. Cl.² ..................... C07C 177/00

[58] Field of Search ............ 260/468 D, 514 D

[56] References Cited

UNITED STATES PATENTS 3,849,474 11/1974 Abraham et al. ............... 260/468

*Primary Examiner*—Robert Gerstl
*Attorney, Agent, or Firm*—Albert H. Graddis; Frank S. Chow

[57] ABSTRACT

15-Cycloalkyl-prostaglandins of the formula:-

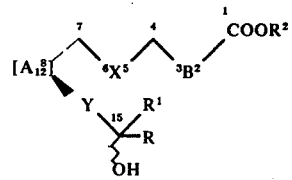

wherein A represents a grouping of the formula:-

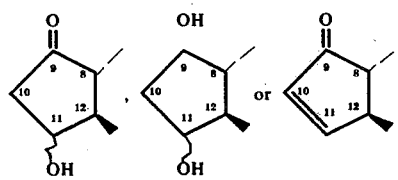

X represents ethylene of cis-vinylene, Y represents ethylene or trans-vinylene, B represents ethylene or trans-vinylene, R represents hydrogen or alkyl of 1 through 4 carbon atoms, $R^1$ represents cycloalkyl of 4 through 7 carbon atoms, and $R^2$ represents hydrogen or alkyl of 1 through 12 carbon atoms, are new compounds possessing the useful pharmacological properties typical of prostaglandins; they are of especial interest in the inhibition of blood platelet aggregation.

7 Claims, No Drawings

15-CYCLOALKYL-PROSTAGLANDINS

THIS INVENTION is concerned with new prostaglandin analogues.

Prostaglandins are derivatives of prostanoic acid which has the following formula:

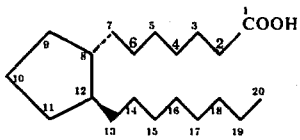

I

Various types of prostaglandins are known, the types depending inter alia on the structure and substituents on the alicyclic ring. For example, the alicyclic rings of prostaglandins E(PGE), F(PGF) and A(PGA) have the structures:

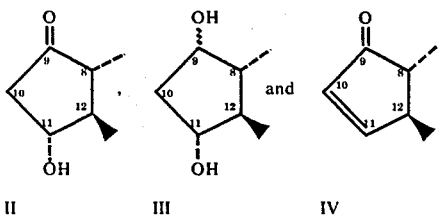

II   III   IV respectively. The dotted lines in the foregoing formulae and in other formulae throught this specification denote, in accordance with generally accepted rules of nomenclature, that the attached grouping lies behind the general plane of the ring system, i.e. that the grouping is an α-configuration, that the thickened lines ▼ denote that the grouping lies in front of the general plane of the system, i.e. that the grouping is in β-configuration, and that the wavy line ∿ indicates that the grouping is in α- or β-configuration.

Such compounds are sub-classified according to the position of double bond(s) in the side chain(s) attached to the 8- and 12-positions of the alicyclic ring. Thus $PG_1$ compounds have a trans-double bond between $C_{13}$–$C_{14}$ (trans-$\Delta^{13}$), $PG_2$ compounds have a cis-double bond between $C_5$–$C_6$ and a trans-double bond between $C_{13}$–$C_{14}$ (cis-$\Delta^5$, trans-$\Delta^{13}$), and $PG_3$ compounds have cis-double bonds between $C_5$–$C_6$ and $C_{17}$–$C_{18}$ and a trans-double bond between $C_{13}$–$C_{14}$ (cis-$\Delta^5$, trans-$\Delta^{13}$, cis-$\Delta^{17}$). For example, prostaglandin $F_{1\alpha}$ ($PGF_{1\alpha}$) and prostaglandin $E_1$ ($PGE_1$) are characterized by the following structures V and VI.

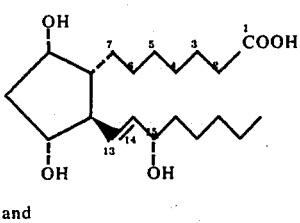

V and

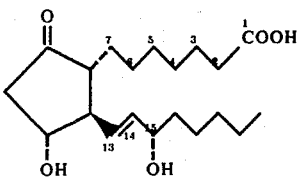

VI respectively. The structures of $PGF_{2\alpha}$ and $PGE_2$, as members of the $PG_2$ group, correspond to those of formulae V and VI respectively with a cis-double bond between the carbon atoms in positions 5 and 6. Compounds in which the double bond between the carbon atoms in positions 13 and 14 of members of the $PG_1$ group is replaced by ethylene (i.e. —$CH_2CH_2$—) are known as dihydro-prostaglandin, e.g. dihydro-prostaglandin-Fα(dihydro-$PGF_{1\alpha}$) and dihydro-prostaglandin-$E_1$ (dihydro-$PGE_1$).

Moreover, when one or more methylene groups are eliminated from the aliphatic group attached to the 12-position of the alicyclic ring of the prostaglandins the compounds are known, in accordance with the usual rules of organic nomenclature, as ω-nor-prostaglandins and, when more than one methylene group is eliminated, the number is indicated by di-, tri- etc. before the prefix "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGEs and PGAs have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGEs and PGFs have 3 stimulating effect on smooth muscle and increase the intestinal peristalsis; these actions indicate therapeutic utility on post-operative ileus and as purgatives. Furthermore, PGFs and PGFs may be used as oxytocics, as abortifacients in the first and second trimesters; in the post-labour abortion of the placenta, and as oral contraceptives because they regulate the sexual cycle of female mammals. PGEs and PGAs have vasodilator and diuretic activities. PGEs are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree. It has now been found that by introducing a cycloalkyl group containing from 4 to 7 carbon atoms on the carbon atom in the 15-position of prostaglandins E, F and A and certain analogues thereof, new prostaglandin analogues are obtained which possess the pharmacological properties of the 'natural' prostaglandins and are, in some aspects of their activities, an improvement, for example they possess an enhanced strength of activity or a prolonged duration of activity.

The present invention accordingly provides the new prostaglandin analogues of the general formula:

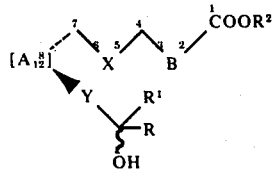
VII (wherein A represents a grouping of formula IV as indicated hereinbefore or a grouping of the formula:

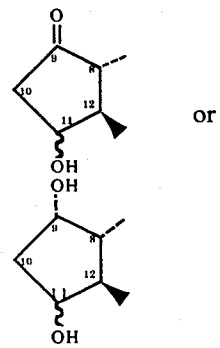
VIIIA or

VIIIB

X represents ethylene (i.e. —CH$_2$CH$_2$—) or cis-vinylene (i.e. —CH=CH—), Y represents ethylene or trans-vinylene, B represents ethylene or trans-vinylene, R represents a hydrogen atom or a straight- or branched-chain alkyl group containing from 1 to 4 carbon atoms, R$^1$ represents a cycloalkyl group containing from 4 to 7 carbon atoms, and R$^2$ represents a hydrogen atom or a straight- or branched-chain alkyl group containing from 1 to 12 carbon atoms, for example methyl) and the corresponding alcohols [i.e. compounds of general formula VII wherein the group COOR$^2$ is replaced by the hydroxymethylene (i.e. —CH$_2$OH) group and the various other symbols are as hereinbefore defined] and cyclodextrin clathrates of such acids, esters and alcohols and, when R$^2$ represents a hydrogen atom, non-toxic (e.g. sodium) salts thereof. Preferably R represents a hydrogen atom or a methyl group, preferably R$^1$ represents a cyclobutyl, cyclopentyl or cyclohexyl group, and preferably the hydroxy groups depicted in formulae VII, VIIIA and VIIIB in α-or β configuration are attached to the carbon atom in α-configuration.

The present invention is concerned with all compounds of general formula VII in the 'natural' form or its enantiomeric form, or mixtures thereof, more particularly the racemic form, consisting of equimolecular mixtures of natural and its enantiomeric form.

As will be apparent to those skilled in the art, the compounds depicted in general formula VII have at least three centers of chirality, these three centers of chirality being at the alicyclic ring carbon atoms of group A identified as 8 and 12 and at the C-15 carbon atom which has attached to it a hydroxy group. Still further centers of chirality ocur when the alicyclic group A carries a hydroxy group on the carbon atom in position 11 (i.e. when the ring is that of formula VIIIA) or hydroxy groups in positions 9 and 11 (i.e. when the ring is that of formula VIIIB). The presence of chirality leads, as is well known, to the existence of isomerism. However, the compounds of general formula VII all have such a configuration that the side-chains attached to the ring carbon atoms in the positions identified as 8 and 12 are trans with respect to each other. Accordingly, all isomers of general formula VII, and mixtures thereof, which have those side-chains attached to the ring carbon atoms in positions 8 and 12 in the trans-configuration and have a hydroxy group as depicted in the 15-position are to be considered within the scope of general formula VII.

According to a feature of the present invention, the prostaglandin analogues of general formula VII, wherein B represents ethylene, R$^2$ represents a hydrogen atom and the other symbols are as hereinbefore defined, are prepared by the process which comprises the hydrolysis to the hydroxy group of the group OR$^3$, and the group OR$^4$ when R$^4$ represents a group as specified hereinafter, of a cyclopentane derivative of the general formula:

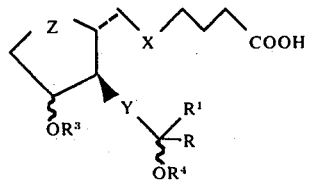
IX

[wherein X, Y, R and R$^1$ are as hereinbefore defined, Z represents

or C=O, and R$^3$ and R$^4$ each represent a 2-tetrahydropyranyl group unsubstituted or substituted by at least one alkyl group, or a 2-tetrahydrofuranyl or 1-ethoxyethyl group (preferably 2-tetrahydropyranyl), or R$^4$ represents a hydrogen atom] to obtain a prostaglandin analogue of the general formula:

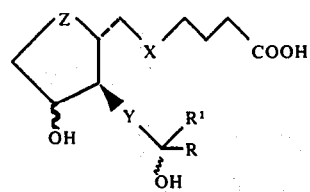
X (wherein the various symbols are as hereinbefore defined) and, if desired, converting by methods known per se the PGE alicyclic ring (Z represents C=O) into that of a PGA (formula IV) compound. By the term "methods known per se" as used in this specifications is meant methods heretofore used or described in the chemical literature.

The group OR$^3$, and the group OR$^4$ when R$^4$ is other than a hydrogen atom, in the cyclopentane derivatives of general formula IX may be converted into the hydroxy group by mild hydrolysis with an aqueous solution of an organic acid, e.g. acetic acid, or with a dilute inorganic acid, e.g. hydrochloric acid, advantageously in the presence of an organic solvent miscible with water, for example tetrahydrofuran or an alcohol containing from 1 to 4 carbon atoms, e.g. methanol. The mild hydrolysis may be carried out at a temperature ranging from ambient to 60° C. (preferably at a temperature below 45° C.) with an acid mixture, e.g. a mixture of acetic acid, water and tetrahydrofuran, or a mixture of hydrochloric acid with tetrahydrofuran or methanol.

The PGE compounds of formula X (Z represents C=O) can be converted into corresponding PGA compounds of general formula VII, wherein A represents a grouping of formula IV, i.e. compounds of the formula:

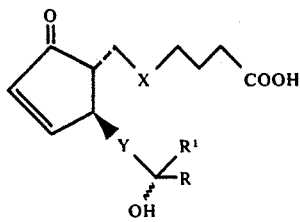

XI (wherein the various symbols are as hereinbefore defined) by methods known per se, for example by subjecting the PGEs to dehydration using an aqueous solution of an organic or inorganic acid having a higher concentration than that employed for hydrolysis of compounds of general formula IX, e.g. IN hydrochloric acid, if desired in the presence of cupric chloride, or acetic acid, and heating at a temperature of 30°–60° C.

It will be appreciated that PGA compounds conforming to general formula VII can be obtained directly from cyclopenetane derivatives of formula IX, wherein Z represents C=O, when such stronger acidic conditions are utilized to hydrolyze the —OR³ group and, when necessary, the —OR⁴ group of starting materials of formula IX as the intermediate PGEs of formula X (Z represents C=O) will then be dehydrated in situ to PGA compounds.

The cyclopentane derivatives of general formula IX employed as starting materials in the aforesaid process are new compounds and as such constitute a feature of the present invention. Those compounds of that formula wherein R represents a hydrogen atom and R⁴ represents a 2-tetrahydropyranyl group unsubstituted or substituted by at least one alkyl group, or a 2-tetrahydrofuranyl or 1-ethoxyethyl group, i.e. a group identical to R³, and X, Y, Z, R¹ and R³ are as hereinbefore defined, can be prepared reacting a bicyclo-octane derivative of the general formula:

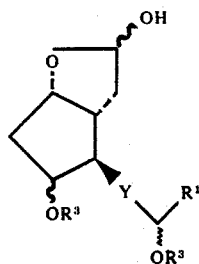

XII (wherein Y, R¹ and R³ are as hereinbefore defined) with 4-carboxy-n-butylidenetriphenylphosphorane of the formula $(C_6H_5)_3P=CH—(CH_2)_3—COOH$ to obtain a cyclopentane derivative of the general formula:

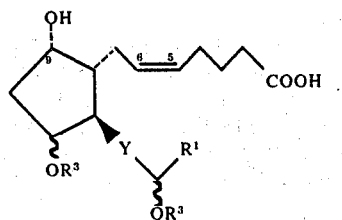

XIII (wherein Y, R¹ and R³ are as hereinbefore defined), optionally hydrogenating by methods known per se the cis-double bond in the $C_5$–$C_6$ position to obtain a corresponding compound of the general formula:

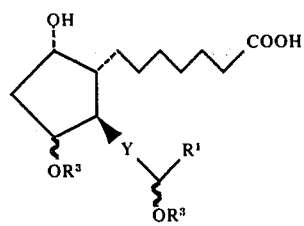

XIV (wherein Y, R¹ and R³ are as hereinbefore defined), and optionally converting by methods known per se the 9β-hydroxy group in the cyclopentane derivatives of general formula XIII or XIV to an oxo radical to obtain a cyclophentane derivative of general formula IX as hereinbefore mentioned.

The reaction between the bicyclo-octanes of general formula XII and 4-carboxy-n-butylidenetriphenylphosphorane [obtained by the reaction of sodiomethylsulphinylcarbanide with 4-carboxy-n-butyltriphenylphosphonium bromide] is carried out under the normal conditions utilized for effecting the Witting reaction, e.g. in an inert solvent at ambient temperature. The reaction is preferably carried out in dimethyl sulphoxide because the phosphonium salt is practically insoluble in other solvents, e.g. tetrahydrofuran, and because a cis-double bond must be formed stereospecifically in the Wittig reaction. For the better performance of the Witting reaction more than two molecular equivalents of the phosphorane compound are required for each mole of the bicyclo-octane reactant. The reaction is generally effected at a temperature of 10°–40° C., preferably at 20°–30° C., and is usually complete after about 30 minutes to four hours at laboratory temperature. The acid product of formula XIII may be extracted from the reaction mixture by conventional procedures and further purified by column chromatography on silica gel.

The cis-double bond in the $C_5C_6$ position of the cyclopentane derivatives of general formula XIII wherein Y is ethylene can be reduced to form an ethylene group, giving compounds of general formula XIV, by hydrogenation in the presence of a hydrogenation catalyst, for example palladium or charcoal, palladium black or platinum dioxide, in the presence of an inert organic solvent, for example a lower alkanol, e.g. methanol or ethanol, at laboratory temperature and at normal or elevated pressure, e.g. at a hydrogen pressure from atmospheric to 15 kilogrammes per square centimeter. The cis-double bond in the $C_5C_6$ position of the cyclopentane derivatives of general formula XII wherein Y is trans—CH=CH— can be reduced, if desired, to form an ethylene group selectively by hydrogenation in the presence of a hydrogenation catalyst, e.g. a palladium catalyst.

The PGF alicyclic ring in the compounds of general formula XIII and XVI can be converted into a PGE ring by methods known per se for the conversion of a hydroxy group in the 9-position of a prostaglandin to an oxo radical, for example by means of a chromic acid solution (e.g. obtained from chromium trioxide, manganese sulphate, sulphuric acid and water) or Nones' reagent.

The bicyclo-octane starting materials of general formula XII can be prepared by the series of reactions depicted schematically below in Scheme A:

enone is treated with excess sodium borohydride in an inert solvent, for example a lower alkanol, e.g. methanol or ethanol, or tetrahydrofuran, at a temperature of −45° C. to −30° C. for about 5 munutes, or with excess zinc borohydride in an inert solvent, e.g. 1,2-dimethoxyethane, at a temperature of −10° C. to 10° C., to reduce the carbonyl group in the side-chain to hydroxymethyl $$(i.e. -\underset{\underset{OH}{|}}{C}H-),$$

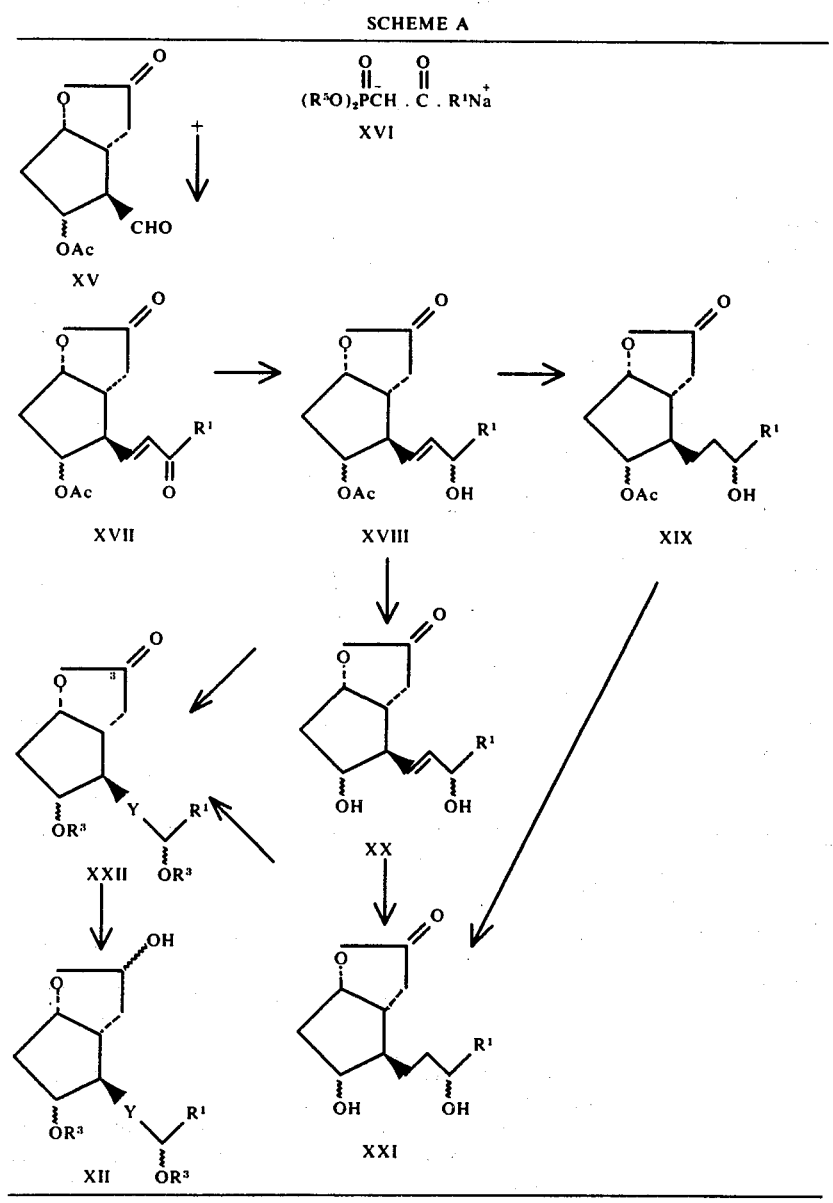

SCHEME A wherein Ac represents the acetyl group, $R^5$ represents the methyl or ethyl group, and Y, $R^1$ and $R^3$ are as hereinbefore defined.

The bicyclo-octane aldehyde of formula XV is reacted with the sodio derivative of a dialkylphosphonate of formula XVI in tetrahydrofuran, for example at a temperature between laboratory temperature and 30° C. for about 1 to 2 hours, to form sterospecifically the trans-enone lactone of general formula XVII. The treatment being carried out at a low temperature, e.g. 10° C. to −45° C., to prevent contemporaneous reduction of the conjugated carboncarbon double bond, and to form a mixture (ratio about 1:1) of the α- and β-hydroxy epimers of the compound of general formula XVIII. If desired, separation of the α- and β-hydroxy epimers may be effected by column chromatography on silica gel using a mixture of diethyl ether-n-hexane-ethyl acetate (5:3:2) as eluent. If desired, a compound of general formula XVIII may be dissolved in a suitable solvent, e.g. methanol or ethanol, and then subjected to catalytic hydrogenation in the presence of a catalyst effective for the reduction of the double bond to form an ethylene group, for example palladium on charcoal, palladium black or platinum dioxide, to give a compound of formula XIX. Deacetylation of compounds of general formulae XVIII and XIX to form, respectively, the diols of general formulae XX and XXI is effected with an equimolecular amount of potassium carbonate in methanol. If desired, the double bond of a compound of general formula XX may be catalytically hydrogenated, as hereinbefore described for the conversion of compounds of general formula XVIII to compounds of general formula XIX, to give a compound of general formula XXI. The compounds of general formulae XX and XXI are then reacted with a dihydropyran, dihydrofuran or ethyl vinyl ether, in an inert organic solvent, e.g. methylene chloride, in the presence of a condensing agent, for example p-toluenesulphonic acid, and the resulting bis-tetrahydropyranyl ether of general formula XXII is reduced at a low temperature, preferably below −50° C., with a reagent capable of reducing the oxo radical in the position indicating as 3 to a hydroxy group, preferably using diisobutylaluminium hydride, for example three molecular equivalents of diisobutylaluminium hydride in toluene at −60° C. for 5 minutes, to give a compound of formula XII.

The compound of formula XV wherein the group OAc is in α-configuration, i.e. 2-oxa-3-oxo-6-synformyl-7-anti-acetoxy-cis-bicyclo[3,3,0]octane, is a known substance whose preparation is disclosed in J. Amer. Chem. Soc., 92, 397 (1970). The compounds of formula XV may be prepared by the oxidation under mild and neutral conditions, e.g. with chromium trioxide-pyridine complex at a moderately low temperature, of a compound of the general formula:

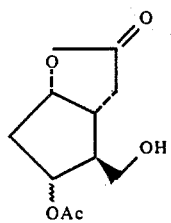

XXIII wherein Ac is as hereinbefore defined.

The racemic form of the compound of formula XXIII is described in J. Amer. Chem. Soc., 91, 5675 (1969) and the natural configuration compound of formula XXXII is described in J. Amer. Chem. Soc., 92, 397 (1970). A method for the preparation of the bicyclooctane starting materials of formula XXIII wherein Ac is as hereinbefore defined and the group OAC is in β-configuration, utilizing known procedures may be represented by the series of reactions depicted schematically below in Chart B (cf. E. J. Corey and Shiro Terashima, Tetrahedron Letters, No. 2, 111-113, 1972):

CHART B

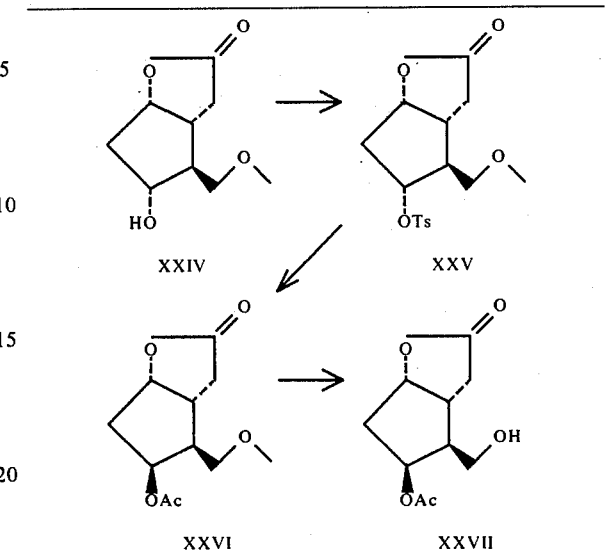

wherein Ac is as hereinbefore defined and Ts represents the tosyl group. The various reactions depicted above in Chart B may be effected by methods known per se. Compounds of formula XXVI may be prepared by reacting compounds of formula XXV with tetraethylammonium acetate.

The sodio derivatives of general formula XVI may be prepared by the dropwise addition of a solution of a compound of the general formula:

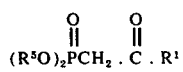

XXVIII (wherein $R^1$ and $R^5$ are as hereinbefore defined) in tetrahydrofuran to a suspension of sodium hydride in tetrahydrofuran under an atmosphere of nitrogen at laboratory temperature.

The compounds of general formula XXVIII may be prepared by reacting a solution of n-butyllithium with a solution of dimethyl methylphosphonate or diethyl methylphosphonate in tetrahydrofuran for about 15 minutes under an atmosphere of nitrogen at a temperature of from −60° C. to −70° C. and then adding, dropwise, to the reaction mixture, a solution of a compound of the general formula:

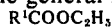   XXIX (wherein $R^1$ is as hereinbefore defined) in tetrahydrofuran at a temperature below −55° C., stirring at −60° C. to −70° C. for 2 hours and then stirring for 16 hours at 0° C. to give the desired product of general formula XXVIII.

The cycloalkanecarboxylic esters of general formula XXIX may be prepared by methods known per se from the corresponding cycloalkanecarboxylic acid.

4-Carboxy-n-butylidenetriphenylphosphorane may be prepared by methods known per se, for example by the procedure described in J. Amer. Chem. Soc., 91, 5675 (1969). Thus, 4-carboxy-n-butylidenetriphenylphosphorane may be prepared by reacting a compound of the general formula:

   XXX wherein Q represents a chlorine or bromine atom, e.g. 4-carboxy-n-butyltriphenylphosphonium bromide, with an alkali metal, e.g. sodium, methylsulphinylcarbanide. The reaction is preferably carried out in an inert solvent, for example, dimethyl sulphoxide, at 25° C. In dimethyl sulphoxide, the phosphorane is formed within a short time and the product is scarlet. The alkali metal methylsulphinylcarbanide may be prepared in situ by reacting an alkali metal, e.g. sodium, hydride with dimethyl sulphoxide at a temperature of from 65° C. to 70° C.

The cyclopentane derivatives of general formula IX employed in the aforementioned process of the present invention, wherein R represents a straight- or branched-chain alkyl group containing from 1 to 4 carbon atoms, $R^4$ represents a hydrogen atom, and X, Y, Z and $R^1$ are as hereinbefore defined, can be prepared by hydrolyzing a cyclopentane derivative of the general formula:

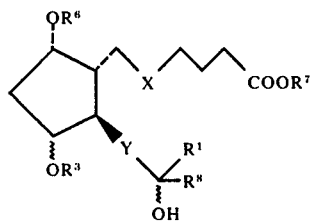  XXXI

[wherein X, Y, $R^1$ and $R^3$ are as hereinbefore defined, $R^6$ represents an alkylcarbonyl group containing from 1 to 4 carbon atoms, $R^7$ represents a straight- or branched-chain alkyl group containing from 1 to 4 carbon atoms (preferably methyl), and $R^8$ represents a straight- or branched-chain alkyl group containing from 1 to 4 carbon atoms] with an aqueous solution of an alkali metal (e.g. sodium or potassium) hydroxide or carbonate in the presence of a water-miscible organic solvent (e.g. tetrahydrofuran or an alkanol containing from 1 to 4 carbon atoms) to obtain a cyclopentane derivative of the general formula:

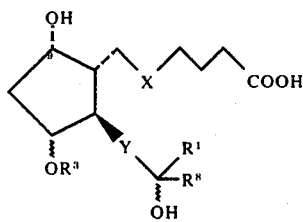  XXXII (wherein the various symbols are as hereinbefore defined), and optionally converting by methods known per se the 9α-hydroxy group in the PGF compound to an oxo radical, for example by means of a chromic acid solution (e.g. obtained from chromium trioxide, manganese sulphate, sulphuric acid and water) or Jones' reagent.

The cyclopentane derivatives of general formula XXXI may be prepared from compounds of the general formula:

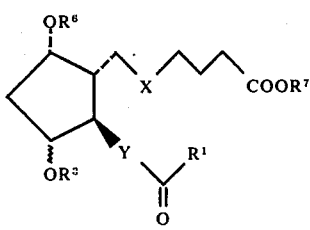  XXXIII (wherein the various symbols are as hereinbefore defined) by treatment with a Grignard reagent of the general formula:

$$R^8-Mg-Hal \qquad XXXIV$$

(wherein $R^8$ is as hereinbefore defined and Hal represents a halogen atom), e.g. methylmagnesium iodide, in an inert organic solvent, for example tetrahydrofuran or diethyl ether, at a moderately low temperature, for example at 0° C., followed by hydrolysis of the resulting organomagnesium prostaglandin compound, for example by treatment with water or an aqueous solution of ammonium chloride or an acid, e.g. hydrochloric acid or oxalic acid, to give a mixture of the α- and β-hydroxy epimers of the compounds of general formula XXXI.

The compounds of general formula XXXIII may be prepared from compounds of the general formula:

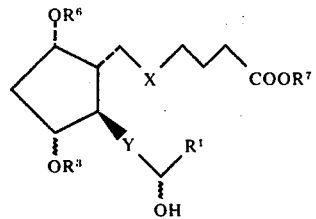  XXXV (wherein the various symbols are as hereinbefore defined) by oxidation with chromium trioxide or manganese dioxide.

Compounds of general formula XXXV may be obtained by the reaction of a compound of the general formula:

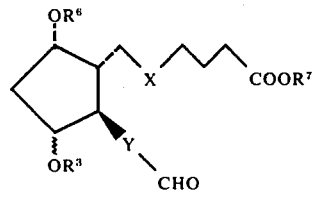  XXXVI (wherein the various symbols are as hereinbefore defined) with an organo-metallic compound of the general formula:

$$Met-R^1 \qquad XXXVII$$

wherein $R^1$ is as hereinbefore defined, and Met represents a lithium atom or a magnesium halide group. The reaction is preferably effected at a low temperature, preferably below 0° C., more particularly in the case of an organolithium compound below −50° C., in an inert organic solvent, e.g. diethyl ether, tetrahydrofuran or n-hexane, for 10 to 60 minutes. The reaction mixture is then hydrolyzed by treatment with water or an aqueous solution of an acid or ammonium chloride to give a compound of general formula XXXVI.

The compounds of general formula XXXVI wherein X represents cis-vinylene, Y represents trans-vinylene, and $R^3$, $R^6$ and $R^7$ are as hereinbefore defined, hereinafter depicted by general formula XXXVIA, can be prepared by the sequences of reactions hereinafter depicted schematically in Chart C.

Referring to Chart C, the starting compounds of general formula XXXVIII may be prepared from the

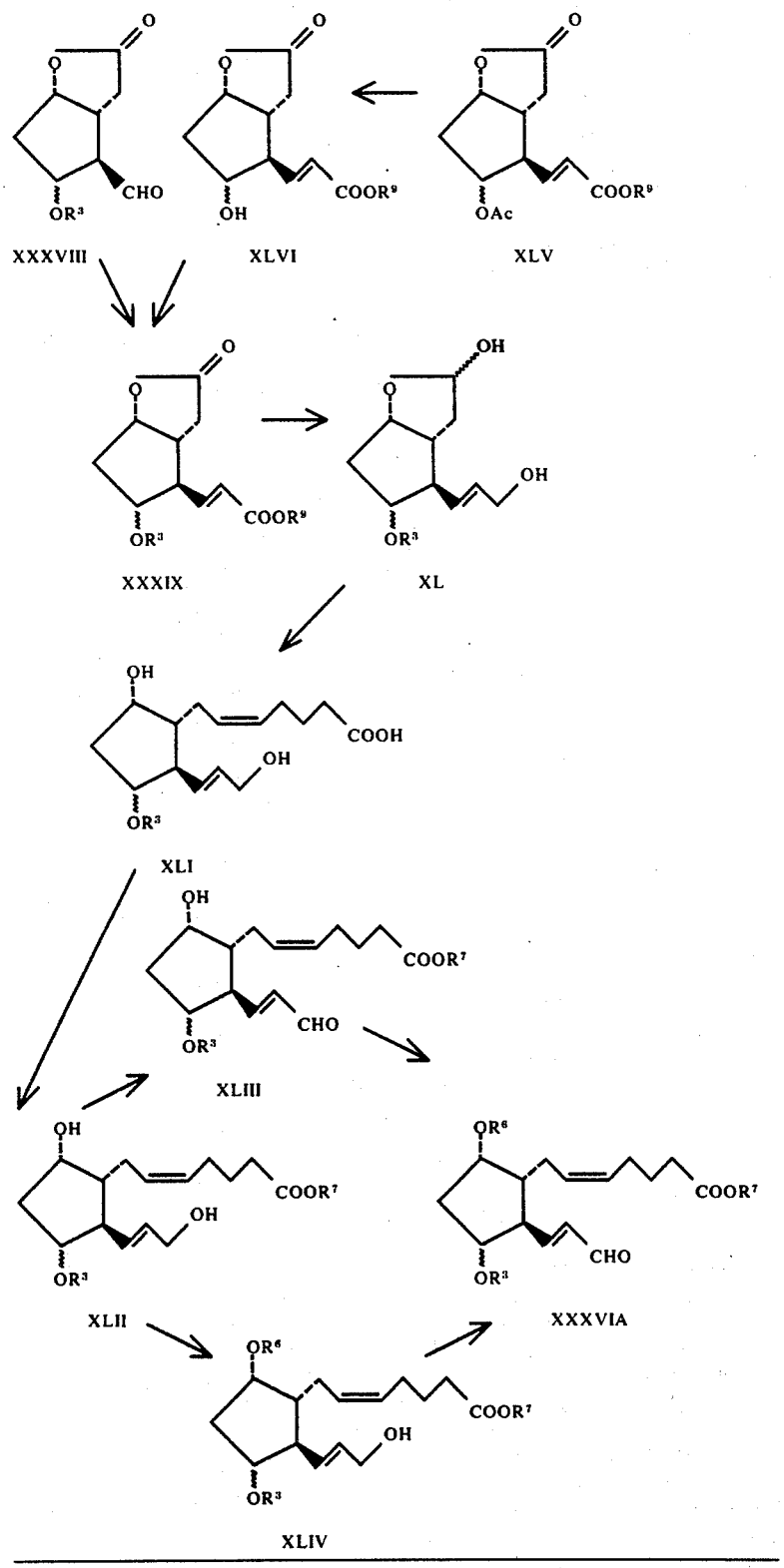

CHART C wherein $R^9$ represents a straight- or branched-chain alkyl group containing from 1 to 4 carbon atoms, and $R^3$, $R^6$, $R^7$ and Ac are as hereinbefore defined.

compounds of general formula XLVII depicted hereafter by the series of reactions depicted schematically below in Chart D:

CHART D

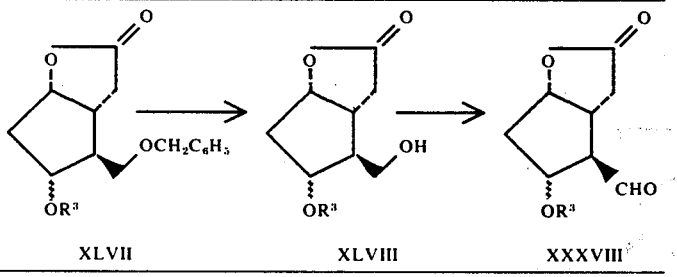

| XLVII | XLVIII | XXXVIII | wherein $R^3$ is as hereinbefore defined.

Compounds of general formula XLVIII may be prepared from compounds of general formula XLVII by catalytic reduction in the presence of a hydrogenation catalyst, for example palladium on charcoal or palladium black, and converted to compounds of general formula XXXVIII by oxidation under mild conditions, e.g. with Collins reagent and at a moderately low temperature.

Compounds of general formula XXXVIII may be transformed stereospecifically to trans-$\alpha,\beta$-unsaturated esters of general formula XXXIX by reaction with the sodio derivative of compounds of general formula:

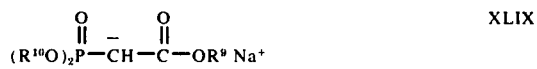

XLIX (wherein $R^9$ is as hereinbefore defined and $R^{10}$ represents an alkyl group containing from 1 to 4 carbon atoms) in an inert organic solvent, e.g. tetrahydrofuran or 1,2-dimethoxyethane, at a temperature of 0° C. to 30° C. for 2 hours, in a high yield, e.g. 70% to 90%.

Compounds of general formula XXXIX may be converted quantitatively to compounds of general formula XL by reduction with more than three molar equivalents of diisobutylaluminium hydride in an inert solvent, e.g. toluene, n-pentane or n-hexane, at a low temperature, e.g. −78° C. to −20° C.

Compounds of general formula XLI may be prepared by the reaction of a compound of general formula XL with a compound of formula:

  L in the presence of a strong base, for example sodiomethylsulphinyl carbanide, under the normal conditions utilized for effecting the Wittig reaction, e.g. in an inert solvent at ambient temperature. The reaction is preferably carried out in dimethyl sulphoxide because the compound of formula L is practically insoluble in other solvents, e.g. tetrahydrofuran, and because a cis-double bond must be formed stereospecifically in the Wittig reaction. For the better performance of the Wittig reaction, more than three equivalents of the phosphorane compound, prepared from the compound of general formula L, are required. Reaction between the compounds of general formula XL and the phosphorane is usually completed in about one to five hours at laboratory temperature. The product of formula XLI, i.e. the acid component of the reaction mixture, may be isolated from the reaction mixture in a high yield by conventional procedures.

Compounds of general formula XLI may be esterified to obtain compounds of general formula XLII by reaction with (a) appropriate diazoalkane compounds, e.g. diazomethane, (b) appropriate alcohols in the presence of dicyclohexyl carbodiimide as condensing agent, or (c) appropriate alcohols following the formation of a mixed acid anhydride by adding a tertiary amine and then a pivaloyl halide or an arylsulphonyl or alkylsulphonyl halide (cf. our British Pat. Nos. 1362956 and 1364125), and then, if desired, converted to compounds of general formula XLIV by reaction with trimethylchlorosilane in an inert organic solvent, for example methylene chloride, in the presence of a base, for example pyridine or a tertiary amine, at a low temperature, e.g. at a temperature at −30° C. to 0° C., then reacting the resulting trimethylsilyl ether with the appropriate acyl halide or acid anhydride in an inert organic solvent, for example methylene chloride, in the presence of a base, for example pyridine or a tertiary amine, at a low temperature, e.g. at a temperature of 0° C. to 30° C., and treating the resulting acyl ether by methods known per se for the removal of the trimethylsilyl group, for example by treatment with an acid; it is preferable not to use a strong acid in order to avoid the risk of the removal of the group $R^3$.

Compounds of general formula XLIV may be converted to compounds of general formula XXXVIA by oxidation with manganese dioxide, for example in an inert solvent, e.g. methylene chloride, at laboratory temperature, which oxidizes an allylic alcohol group selectively.

Compounds of general formula XXXVIA can be prepared from compounds of general formula XLII by oxidation with manganese dioxide, for example in an inert organic solvent, e.g. methylene chloride, at laboratory temperature, and then acylation via compounds of general formula XLIII.

Compounds of general formula XXXIX can also be prepared from compounds of general formula XLV by selective deacetylation with an equimolar amount of anhydrous potassium carbonate in absolute methanol and then etherification of the resulting compound of general formula XLVI with a dihydropyran, dihydrofuran or ethyl vinyl ether in an inert organic solvent, such as methylene chloride, in the presence of a condensing agent, for example p-toluenesulphonic acid.

Compounds of general formula XLVII may be prepared by known methods, for example as described in J. Org. Chem. 37, 2921 (1972) for the preparation of a compound of general formula XLVII wherein $R^3$ is a 2-tetrahydropyranyl group.

Compounds of general formula XXXVI wherein x and Y represent ethylene may be obtained by reduction of compounds of general formula XXXVI wherein X and Y represent vinylene by means of diimide, which is prepared from hydrazine and an oxidizing agent, for example hydroperoxide [cf. J. Chem. Ed. 42, 254 (1965)]. Compounds of general formula XXXVI wherein X represents cis-vinylene and Y represents ethylene may be obtained by the selective reduction of the carbonyl conjugated double bond Y of compounds of general formula XXXVI wherein X represents cis-vinylene and Y represents trans-vinylene by methods known per se, for example by means of lithium-1-pentyne-hydrocuprate (LiCuH—C—CC₃H₇).

The compounds of general formula XXXVII, wherein Met represents magnesium halide, may be prepared by reacting magnesium with a compound of the general formula:

Hal — R¹  LI wherein Hal represents a halogen atom and R¹ is as hereinbefore defined.

According to a further feature of the present invention, the prostaglandin analogues of general formula VII, wherein B represents trans-vinylene and the other symbols are as hereinbefore defined, are prepared by the process which comprises hydrolysing to hydroxy groups the OR³ groups of a cyclopentane derivative of the general formula:

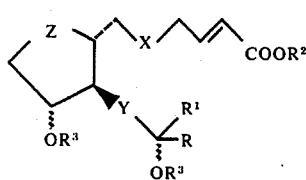  LII (wherein the various symbols are as hereinbefore defined) to obtain a prostaglandin compound of the general formula:

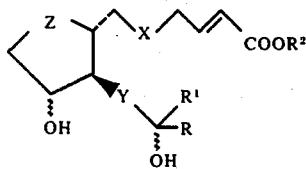  LIII (wherein the various symbols are as hereinbefore defined) and, if desired, converting by methods known per se the PGE alicyclic ring (Z represents C=O) into that of a PGA (formula IV) compound.

Hydrolysis to hydroxy groups of the groups —OR³ of compounds of general formula LII may be effected as hereinbefore described for the conversion to the hydroxy group of the group OR³, and the group OR⁴ when R⁴ is other than a hydrogen atom, of the cyclopentane derivatives of general formula IX.

Compounds of general formula LII wherein Z represents C=O may be prepared from the corresponding compounds of general formula LII wherein Z represents

by methods known per se for the conversion of a hydroxy group in the 9-position of a prostaglandin to an oxo radical, for example by means of a chromic acid solution (e.g. obtained from chromium trioxide, manganese sulphate, sulphuric acid and water) or Jones' reagent.

The PGE compounds of general formula LIII (Z represents C=O) can be converted into corresponding PGA compounds by methods known per se, for example as hereinbefore described for the conversion of compounds of formula X (Z represents C=O) into the corresponding PGA compounds of formula XI.

Compounds of general formula LII wherein Z represents

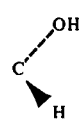

and the other symbols are as hereinbefore defined, i.e. compounds of general formula:

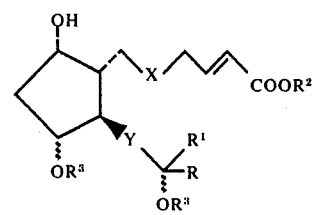  LIV (wherein the various symbols are as hereinbefore defined) may be prepared by reacting a compound of the general formula:

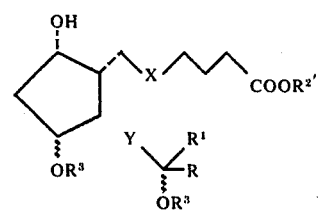  LV (wherein X, Y, R, R¹ and R³ are as hereinbefore defined and R²′ represents a straight- or branched-chain alkyl group containing from 1 to 12 carbon atoms) with (1) a lithium dialkylamide, e.g. lithium diisopropylamide or lithium cyclohexylisopropylamide, to form a lithium enolate, followed successively by (2) treatment with 2 to 4 molecular equivalents of phenylselenyl bromide (C₆H₅SeBr), diphenyldiselenide (C₆H₅SeSeC₆H₅) or a dialkyldisulphide or diphenyldisulphide at a temperature of from −70° C. to laboratory temperature in an inert organic solvent, e.g. tetrahydrofuran, diethyl ether, n-hexane or n-pentane or mixtures thereof, (3) treatment with a small amount of a saturated aqueous ammonium chloride solution, (4) extraction with an organic solvent and (5) treatment of the organic extracts with 3 to 7 molecular equivalents of hydrogen peroxide or sodium periodate with a lower alkanol or ethyl acetate at a temperature from 0° C. to laboratory temperature, to give a product of the general formula:

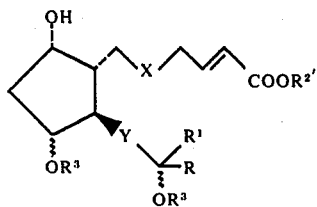

LVI wherein the various symbols are as hereinbefore defined.

When a dialkyldisulphide or diphenyldisulphide is used in step (2), the product of step (5) should be further heated at a temperature of from 50° C. to 120° C. in the presence of a small amount of calcium carbonate.

Compounds of general formula LVI, which are compounds of formula LIV wherein $R^2$ represents a straight- or branched-chain alkyl group containing from 1 to 12 carbon atoms, may, if desired, be converted to the corresponding compounds of formula LIV wherein $R^2$ represents a hydrogen atom (a) by treatment with bakers' yeast [cf. C. J. Sih et al, J. Amer. Chem. Soc., 94, 3643–3644 (1972)] or (b) when X is ethylene, hydrolysis under alkaline conditions, for example by treatment with an aqueous solution of an alkali metal, e.g. sodium or potassium, hydroxide or carbonate, optionally in the presence of an organic solvent, e.g. methanol, ethanol, tetrahydrofuran, 1,2-dimethoxyethane or dimethyl sulphoxide or mixtures thereof, at a temperature between 0° C. and laboratory temperature, to give compounds of general formula LIV wherein $R^2$ represents a hydrogen atom and the other symbols are as hereinbefore defined.

Compounds of general formula LV may be prepared by the esterification of corresponding compounds wherein $R^{2\prime}$ represents a hydrogen atom by procedures herein disclosed for the esterification of compounds of general formula XLI.

The acids corresponding to compounds of general formula LV wherein R represents a hydrogen atom (cf. formula IX) can be obtained by procedures hereinbefore described. The acids corresponding to compounds of general formula LV wherein R represents an alkyl group containing from 1 to 4 carbon atoms can be obtained by treatment of cyclopentane derivatives of general formula XXXI with a dihydropyran, dihydrofuran or ethyl vinyl ether, in an inert organic solvent, e.g. methylene chloride, in the presence of a condensing agent, e.g. p-toluenesulphonic acid, followed by hydrolysis of the resulting compound of the general formula:

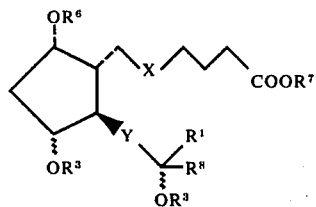

LVII (wherein the various symbols are as hereinbefore defined) by means heretofore disclosed for the hydrolysis of compounds of general formula XXXI to compounds of general formula XXXII.

According to a further feature of the present invention, the compounds of general formula VII wherein A, X, Y, B, R and $R^1$ are as hereinbefore defined and $R^2$ represents a straight- or branched-chain alkyl group containing from 1 to 12 carbon atoms, are prepared by esterification of the corresponding compounds of formula VII wherein $R^2$ represents a hydrogen atom by methods known per se, for example by reaction with (i) the appropriate diazoalkane in an inert organic solvent, e.g. diethyl ether, at a temperature of from −10° C. to 25° C. and preferably 0° C., (ii) the appropriate alcohol or thiol in the presence of dicyclohexylcarbodiimide as condensing agent, or (iii) the appropriate alcohol following formation of a mixed anhydride by adding a tertiary amine and pivaloyl halide or an alkylsulphonyl halide (cf. our British Pat. Nos. 1362956 and 1364125).

Compounds of general formula VII wherein $R^2$ represents a hydrogen atom may, if desired, be converted by methods known per se into non-toxic salts.

By the term 'non-toxic salts', as used in this specification, is meant salts the cations of which are relatively innocuous to the animal organism when used in therapeutic doses so that the beneficial pharmacological properties of the compounds of general formula VII are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acid are well known and include, for example amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The non-toxic salts may be prepared from compounds of general formula VII wherein $R^2$ represents a hydrogen atom by, for example, reaction of stoichiometric quantities of an acid of general formula VII and the appropriate base, e.g. an alkali metal hydroxide or carbonate, ammonium hydroxide, ammonia or an amine, in a suitable solvent. The salts may be isolated by lyophilisation of the solution, or, if sufficiently insoluble in the reaction medium, by filtration, if necessary after removal of part of the solvent.

The prostaglandin alcohols of the present invention [i.e. compounds of formula VII wherein the group $COOR^2$ is replaced by the hydroxymethylene (i.e. $-CH_2OH$) group and the various other symbols are as hereinbefore defined] can be prepared from the acids of general formula VII by application of the method described by Pike, Lincoln and Schneider in J. Org. Chem. 34, 3552–3557 (1969), for example by converting the acids of general formula VII into their methyl esters and then the esters into oximes and reducing the oximes with lithium aluminum hydride to form oxime alcohols, and hydrolyzing them with, for example, acetic acid. PGF alcohols can also be obtained directly by reducing methyl esters of PGF compounds of general formula VII with lithium aluminium hydride.

Cyclodextrin clathrates of compounds of general formula VII and the corresponding alcohols may be prepared by dissolving the cyclodextrin in water or an organic solvent which is miscible with water and adding to the solution the cyclopentane derivative in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70° C. during the preparation of the cyclodextrin clathrates. α-, β- or γ-Cyclodextrins or mixtures thereof may be used in the preparation of the cyclodextrin clathrates. Conversion into their cyclodextrin clathrates serves to increase the stability of the cyclopentane derivatives.

The cyclopentane compounds of general formula VII and the corresponding alcohols and their cyclodextrin clathrates and, when $R^2$ in formula VII represents a hydrogen atom, their non-toxic salts, possess the valuable pharmacological properties typical of prostaglandins in a selective fashion, in particular hypotensive activity, inhibitory activity on blood platelet aggregation, inhibitory activity on gastric acid secretion and gastric ulceration, bronchodilator activity, abortifacient activity and stimulatory activity on uterine contraction, luteolytic activity and antinidatory activity, and are useful in the treatment of hypertension, in the treatment of disorders of the peripheral circulation, in the prevention and treatment of cerebral thrombosis and myocardial infarction, in the treatment of gastric ulceration, in the treatment of asthma, in the termination of pregnancy and induction of labour in pregnant female mammals, in the control of oestrus in female mammals and in the prevention of pregnancy in female mammals. For example, by intravenous administration to the allobarbital-anaesthetized dog, 15(S)-cyclohexyl-ω-pentanor-$PGE_2$ produces falls in blood pressure of 14 mm.Hg, 18 mm.Hg, and 32 mm.Hg lasting 10 minutes, 11 minutes and 16 minutes respectively at doses of 10, 20 and 50 μg./kg. animal body weight respectively, 15(S)-cyclohexyl-ω-pentanor-$PGA_2$ produces falls in blood pressure of 16 mm.Hg, 22 mm.Hg and 24 mm.Hg lasting 12 minutes, 14 minutes and 14 minutes respectively at doses of 0.2, 0.5 and 1.0 μg./kg. animal body weight respectively, 15(S)-cyclohexyl-ω-pentanor-$PGE_1$ produces falls in blood pressure of 20 mm.Hg and 38 mm.Hg lasting 3 minutes and 6 minutes respectively at doses of 1 and 2 μg./kg. animal body weight respectively, 15(S)-cyclobutyl-ω-pentanor-$PGE_2$ produces falls in blood pressure of 18 mm.Hg and 22 mm.Hg lasting 7 minutes and 13 minutes respectively at doses of 5 and 10 μg./kg. animal body weight respectively, 15(S)-cyclobutyl-ω-pentanor-$PGE_1$ produces falls in blood pressure of 12 mm.Hg and 36 mm.Hg lasting 4 minutes and 7 minutes respectively at doses of 1 and 2 μg./kg. animal body weight respectively, 15(S)-cyclobutyl-ω-pentanor-$PGA_2$ produces falls in blood pressure of 22 mm.Hg, 36 mm.Hg and 50 mm.Hg lasting 7 minutes, 9 minutes and 14 minutes respectively at doses of 0.5, 1 and 2 μg./kg. animal body weight respectively, 15(S)-cyclopentyl-ω-pentanor-$PGE_2$ produces falls in blood pressure of 14 mm.Hg and 34 mm.Hg lasting 4 minutes and 7 minutes respectively at doses of 1 and 2 μg./kg. animal body weight respectively, 15(S)-cyclopentyl-ω-pentanor-$PGE_1$ produces falls in blood pressure of 22 mm.Hg and 44 mm. Hg lasting 3 minutes and 6 minutes respectively at doses of 1 and 2 μg./kg. animal body weight, 15(S)-cyclohexyl-ω-pentanor-trans-$\Delta^2$-$PGE_1$ produces falls in blood pressure of 26 mm.Hg and 64 mm.Hg lasting 7 minutes and 19 minutes respectively at doses of 1 and 2 μg./kg. animal body weight respectively, 15($\xi$)-cyckohexyl-ω-tetranor-$PGE_2$ produces falls in blood pressure of 24 mm.Hg and 36 mm.Hg lasting 14 minutes and 13 minutes respectively at doses of 5 and 10 μg./kg. animal body weight respectively, 15($\xi$)-cyclohexyl-ω-tetranor-$PGE_1$ produces falls in blood pressure of 26 mm.Hg, 30 mm.Hg and 58 mm.Hg lasting 3 minutes, 6 minutes and 31 minutes respectively at doses of 0.5 μg., 1 μg. and 5 μg./kg. animal body weight respectively and 15(S)-cyclopentyl-ω-pentanor-trans-$\Delta^2$-$PGE_1$ produces falls in blood pressure of 36 mm.Hg and 60 mm.Hg lasting 3 minutes and 3 minutes respectively at doses of 1 μg. and 2 μg./kg. animal body weight respectively; 15(S)-cyclohexyl-ω-pentanor-$PGE_1$ produces a 50% inhibition of adenosine diphosphate-induced blood platelet aggregation in platelet-rich plasma of rats at a concentration of $3.1 \times 10^{-3}$ μg./ml. and a 50% inhibition of adenosine diphosphate-induced blood platelet aggregation in platelet-rich plasma of man at a concentration of $1.1 \times 10^{-3}$ μg./ml. in comparison with controls, 15(S)-cyclobutyl-ω-pentanor-$PGE_1$ produces a 50% inhibition of adenosine diphosphate-induced blood platelet aggregation in platelet-rich plasma of rats, rabbits and man at concentrations of $8.8 \times 10^{-3}$ μg./ml., $1.1 \times 10^{-2}$ μg./ml. and $4.0 \times 10^{-4}$ μg./ml., respectively, in comparison with controls, 15(S)-cyclohexyl-ω-pentanor-trans-$\Delta^2$-$PGE_1$ produces a 50% inhibition of adensoine diphosphate-induced blood platelet aggregation in platelet-rich plasma of rats, rabbits and man at concentrations of $3.6 \times 10^{-3}$ μg./ml., $6.4 \times 10^{-3}$ μg./ml. and $5.0 \times 10^{-4}$ μg./ml., respectively, in comparison with controls, 15(S)-cyclopentyl-ω-pentanor-$PGE_1$ produces a 50% inhibition of adenosine diphosphate-induced blood platelet aggregation in platelet-rich plasma of rats and man at concentrations of $3.0 \times 10^{-2}$ μg./ml. and $4.7 \times 10^{-4}$ μg./ml., respectively, in comparison with controls, 15($\xi$)-cyclohexyl-ω-tetranor-$PGE_1$ produces a 50% inhibition of adenosine diphosphate-induced blood platelet aggregation in platelet-rich plasma of rats at a concentration of $2.65 \times 10^{-1}$ μg./ml. in comparison with controls and 15(S)-cyclopentyl-ω-pentanor-trans-$\Delta^2$-$PGE_1$ produces a 50% inhibition of adenosine diphosphate-induced blood platelet aggregation in platelet-rich plasma of rats and man at concentrations of $1.20 \times 10^{-2}$ μg./ml. and $1.17 \times 10^{-3}$ μg./ml., respectively, in comparison with controls, while 15(S)-cyclobutyl-ω-pentanor-$PGE_1$, 15(S)-cyclopentyl-ω-pentanor-$PGE_1$ and 15(S)-cyclohexyl-ω-pentanor-trans-$\Delta^2$-$PGE_1$, when administered by intravenous perfusion over a period of 10 minutes to the urethane-anaesthetized rabbit, produce a 50% reduction in the number of white thrombi, formed by damage with a needle to the wall of the mesenteric artery, at doses of 2.0, 1.68 and 0.50 μg./kg. animal body weight/minute respectively in comparison with controls; in stress ulceration of rats produced according to the method of Takagi and Okabe [Jap. J. Pharmac. 18, 9-18, (1968)], 15(S)-cyclohexyl-ω-pentanor-$PGE_1$ produces 70.68% and 76.05% inhibition of stress ulceration at doses of 2000 and 5000 μg./kg. animal body weight respectively, 15(S)-cyclohexyl-ω-pentanor-$PGE_2$ produces 34.95% and 50.77% inhibition of stress ulceration at doses of 1000 and 2000 μg./kg. animal body weight respectively, 15(S)-cyclopentyl-ω-pentanor-$PGE_1$ produces 61.83% and 65.10% inhibition of stress ulceration at doses of 1000 and 2000 μg./kg. animal body weight respectively, 15(S)-cyclohexyl-ω-pentanor-trans-$\Delta^2$-

PGE$_1$ produces 7.58% and 64.55% inhibition of stress ulceration at doses of 1000 and 2000 μg./kg. animal body weight respectively, and 15(S)-cyclopentyl-ω-pentanor-trans-Δ$^2$-PGE$_1$ produces 31.10% and 56.10% inhibition of stress ulceration at doses of 1000 and 2000 μg./kg. animal body weight respectively, by oral administration; 15(S)-cyclohexyl-ω-pentanor-PGE$_1$, 15(S)-cyclopentyl-ω-pentanor-PGE$_1$ and 15(S)-cyclohexyl-ω-pentanor-trans-Δ$^2$-PGE$_1$ produce an increase in gastric acid pH from 2.0–2.5 to at least 4.0 in 50% of pentagastrin-treated rats when perfused into the stomach at rates of 4.45 (confidence limit 2.7–7.32), 2.7 (confidence limit 1.44–5.04) and 3.30 (confidence limit 1.7–6.4) μg./animal/minute, respectively; against the increase in resistance in the respiratory tract of the guinea-pig induced by the administration of histamine, as determined by the methods of Konzett and Rossler [Arch. exp. Path. Pharmak., 195, 71–74 (1940)], by intravenous administration, 15(S)-cyclohexyl-ω-pentanor-PGE$_2$ produces inhibitions of 50.1%, 51.3% and 60.7% at doses of 2.0, 5.0 and 10.0 μg./kg. animal body weight respectively, 15(S)-cyclohexyl-ω-pentanor-PGE$_2$ produces inhibitions of 23.3%, 50.0% and 90.0% at doses of 0.1, 0.05 and 1.0 μg./kg. animal body weight respectively, 15(S)-cyclopentyl-ω-pentanor-PGE$_1$ produces inhibitions of 60.4% and 66.7% at doses of 1.0 and 2.0 μg./kg. animal body weight respectively, 15(S)-cyclobutyl-ω-pentanor-PGE$_1$ produces inhibitions of 81% and 74% at doses of 0.5 and 1.0 μg./kg. animal body weight respectively, and 15(S)-cyclohexyl-ω-pentanor-PGE$_2$ produces inhibitions of 50.1%, 51.3% and 60.7% at doses of 2, 5 and 10 μg./kg. animal body weight respectively; in their inhibitory effect on histamineinduced contractile response of guinea-pig tracheal muscle, in vitro, 15(S)-cylobutyl-ω-pentanor-PGE$_1$, 15(S)-cyclopentyl-ω-pentanor-PGE$_1$ and 15(S)-cylohexyl-ω-pentanor-PGE$_1$ have PD$_2$ values of 6.08±0.16, 6.42±0.05 and 5.95±0.23 respectively; in prolongation of the pre-convulsion time when a histamine-containing aerosol is administered to the conscious guinea-pig, 15(S)-cyclopentyl-ω-pentanor-PGE$_2$ produces increases in the pre-convulsion time of 65%, 96% and 142% when administered in aerosols generated from solutions containing 10, 100 and 300 μg./ml. of the prostaglandin compound respectively, and 15(S)-cyclopentyl-ω-pentanor-PGE$_1$ produces increases in the pre-convulsion time of 64%, 85%, 186% and 172% when administered in aerosols generated from solutions containing 3, 10, 100 and 300 μg./ml. of the prostaglandin compound respectively; when administered subcutaneously twice daily at a dose of 25 μg./kg. animal body weight to hysterectomised Wistar-strain female rats, 15(S)-cyclohexyl-ω-pentanor-PGF$_2$ exhibits luteolytic activity, producing a 42.9% efficacy in restoring oestrus in comparison with controls within a period of 5.2±0.4 days posthysterectomy, the corresponding period for the controls being 10.9±0.7 days post-hysterectomy; 15(S)-cyclobutyl-ω-pentanor-PGF$_2$ inhibits implantation in pregnant female rats when administered subcutaneously on the 3rd, 4th and 5th days of pregnancy at daily doses of 2000 μg./kg. animal body weight and 15(S)-cyclobutyl-ω-pentanor-PGE$_2$ 15(S)-cyclohexyl-ω-pentanor-PGE$_2$ 15(S)-cyclopentyl-ω-pentanor-PGE$_2$, 15(S)-cyclobutyl-ω-pentanor-PGF$_2$ , 15(S)-cyclopentyl-ω-pentanor-PGF$_2$ and 15(S)-cyclohexyl-ω-pentanor-PGF$_2$ stimulate uterine contraction in the pregnant female rat when administered intravenously on the 20th day of gestation at doses of 20, 50, 50, <50, 50–100 and 50–100 μg./kg. animal body weight respectively. The prostaglandin compounds of the present invention and their cyclodextrin clathrates and non-toxic salts possess relatively low potencies in inducing diarrhoea in comparison with their potencies in respect of the valuable properties hereinbefore described; for example the doses by oral administration of 15(S)-cyclohexyl-ω-pentanor-PGE$_2$, 15(S)-cyclohexyl-ω-pentanor-PGE$_1$, 15(S)-cyclopentyl-ω-pentanor-PGE$_2$, 15(S)-cylopentyl-ω-pentanor-PGE$_1$, 15(S)-cyclohexyl-ω-pentanor-trans-Δ$^2$-PGE$_1$, 15(S)-cyclobutyl-ω-pentanor-PGE$_2$, 15(S)-cyclobutyl-ω-pentanor-PGE$_1$ and 15(S)-cyclopentyl-ω-pentanor-trans-Δ$^2$-PGE$_1$ required to produce diarrhoea in 50% of mice so treated are 15.5, >50, 14.0, 38.0, > 20, 40, 20 and >10 mg./kg. animal body weight respectively.

Compounds of general formula VII of outstanding importance are 15(S)-cyclohexyl-ω-pentanor-PGE$_1$, 15(R)- and 15(S)-cyclobutyl-ω-pentanor-PGE$_1$, 15(S)-cyclohexyl-ω-pentanor-trans-Δ$^2$-PGE$_1$ and its methyl ester, 15(S)-cyclopentyl-ω-pentanor-PGE$_1$ and, especially, 15(S)-cyclopentyl-ω-pentanor-trans-Δ$^2$-PGE$_1$. They are of particular interest in the inhibition of blood platelet aggregation.

The following Reference Examples and Examples illustrate the process of the present invention and products thereof. In the Examples 'IR', 'NMR', 'UV' and 'TLC' represent respectively 'Infrared absorption spectrum', 'Nuclear magnetic resonance spectrum', 'Ultraviolet absorption spectrum' and 'Thin layer chromatography'.

REFERENCE EXAMPLE 1

Dimethyl 2-oxo-2-cyclohexylethylphosphonate

A solution of n-butyllithium was prepared from 21 g. of lithium, 206 g. of n-butyl bromide and 1.1 liters of diethyl ether, and cooled to below −55° C. 150 g. of dimethylmethylphosphonate in 1.2 liters of tetrahydrofuran were added to the solution under an atmosphere of nitrogen at −60° C. and stirred for 15 minutes at −60° to −70° C.

To the solution thus obtained, 94 g. of cyclohexanecarboxylic acid ethyl ester (prepared as described in Beilstein vol. 9, 8) in 600 ml. of tetrahydrofuran were added dropwise keeping the temperature below −55° C. and stirred at −60° to −70° C. for 2 hours and then for 16 hours at 0° C. The reaction mixture was adjusted to pH 4 to 5 and concentrated. The residue was treated with 3 liters of diethyl ether, washed with water, dried and concentrated. The resultant product was subjected to distillation in vacuo, to give 66 g. of the title compound as an oil having the following physical characteristics:

b.p. 121° to 126° C./0.23 to 0.27 mm.Hg;
IR (liquid film); : 2930, 2850, 1707, 1445, 1320, 1260, 1190, 1060, 1035, 1010, 900, 870, 845 and 815 cm$^{-1}$; NMR (CCl$_4$ solution); δ: 3.74 (6H, d), 3.20 (2H, d), 3.0 − 2.2 (1H, m).

REFERENCE EXAMPLE 2

2-Oxa-3-oxo-6-syn-(3-oxo-3-cyclohexyl-prop-trans-1-enyl)-7-anti-acetoxy-cis-bicyclo[3,3,0]octane Under an atmosphere of nitrogen, 146 g. of chromium trioxide were added to 235 ml. of pyridine and 3 liters of methylene chloride, stirred at room temperature for 15 minutes and allowed to cool to −2° to −3° C. 52 g. of 2-oxa-3-oxo-6-syn-hydroxymethyl-7-anti-acetoxy-cis-bicyclo[3,3,0]octane [prepared as described in J. Amer. Chem. Soc. 92, 397, (1970)] in 200 ml. of methylene chloride were then added. The reaction mixture was stirred at −2° to −3° C. for 10 minutes. The solution was filtered and the filtrate was concentrated at 0° C. under reduced pressure.

7.0 g. of sodium hydride (65% content) were dissolved in 1.2 liters of tetrahydrofuran and stirred at room temperature under an atmosphere of nitrogen. To the solution there was added dropwise 44 g. of dimethyl 2-oxo-2-cyclohexylethylphosphonate (prepared as described in Reference Example 1) in 200 ml. of tetrahydrofuran and stirred for 20 minutes until evolution of hydrogen ceased. The aldehyde solution prepared as described above was added to the reaction mixture and stirred for 1 hour at room temperature. After completion of the reaction, the solution was acidified with acetic acid and filtered. The filtrate was concentrated. The residue was subject to column chromatography on silica gel using benzene:ethyl acetate (4:1 to 2:1) as eluent to give 31 g. of the pure title compound having the following physical characteristics:

IR (liquid film); $\nu$: 3020, 2930, 2850, 1775, 1740, 1690, 1665, 1630, 1445, 1420, 1375, 1325, 1295, 1240, 1180, 1075, 975 and 760 cm$^{-1}$;

NMR (CDCl$_3$ solution); $\delta$: 6.80 (1H, d-d), 6.34 (1H, d), 5.4 − 4.9 (2H, m), 2.03 (3H, s);

TLC (developing solvent benzene-ethyl acetate = 4:1); Rf = 0.32.

REFERENCE EXAMPLE 3

2-Oxa-3-oxo-6-syn-[3(S)-hydroxy-3-(S)-cyclohexyl-proptrans-1-enyl]-7-anti-acetoxy-cis-bicyclo[3,3,0]octane 31 g. of 2-oxa-3-oxo-6-syn-(3-oxo-3-cyclohexylprop-trans-1-enyl)-7-anti-acetoxy-cis-bicyclo[3,3,0]-octane (prepared as described in Reference Example 2) in 400 ml. of a mixture of methanol and tetrahydrofuran (1:1) were cooled to −40° to −45° C. 11 g. of sodium borohydride were then added. After stirring for 5 minutes, the reaction mixture was neutralized with oxalic acid at −30° C., allowed to warm to room temperature and concentrated. The residue was mixed with water and ethyl acetate, extracted with ethyl acetate, washed, dried and concentrated. The resultant product was subjected to column chromatography on silica gel using diethyl ether:n-hexane:ethyl acetate (5:3:2) as eluent to give 8 g. of the title 3(S)-compound, 6.2 g. of the corresponding 3(R)-compound and 4 g. of a mixture of them, as crystals. The title compound has the following physical characteristics:

m.p. 100.5° to 101.5° C.;

IR (KBr tablet); $\nu$: 3450, 2925, 2875, 2850, 1770, 1740; 1380, 1255, 1175, 1080, 1005 and 980 cm$^{-1}$;

NMR (CDCl$_3$ solution); $\delta$: 5.65 − 5.25 (2H, m), 5.2 − 4.55 (2H, m), 3.95 − 3.5 (1H, m), 2.0 (3H, s);

TLC (developing solvent benzene:ethyl acetate = 2:3); Rf = 0.57.

REFERENCE EXAMPLE 4

2-Oxa-3-oxo-6-syn-[3(S)-hydroxy-3(S)-cyclohexyl-proptrans-1-enyl]-7-anti-hydroxy-cis-bicyclo[3,3,0]octane 8 g. of 2-oxa-3-oxo-6-syn-[3(S)-hydroxy-3-(S)-cyclohexyl-prop-trans-1-enyl]-7-anti-acetoxy-cis-bicyclo[3,3,0]octane prepared as described in Reference Example 3), 3.2 g. of potassium carbonate and 100 ml. of methanol were mixed and stirred at room temperature for 10 minutes. The reaction mixture was adjusted to pH 3 with 2N hydrochloric acid, 500 ml. of water were added and the solution extracted with ethyl acetate. The extract was washed with an aqueous sodium bicarbonate solution, dried and concentrated under reduced pressure to give 6.7 g. of the title compound as crystals having the following characteristics:

m.p. 108° to 109° C.;

IR (KBr tablet); $\nu$: 3450, 3375, 2910, 2850, 1760, 1355, 1315, 1175, 1160, 1090, 1040, 1010 and 975 cm$^{-1}$;

NMR (CDCl$_3$ solution); $\delta$: 5.7 − 5.3 (2H, m), 5.1 − 4.6 (1H, m);

TLC (developing solvent benzene:ethyl acetate = 2:3); Rf = 0.27.

REFERENCE EXAMPLE 5

2-Oxa-3-oxo-6-syn-[3(S)-(2-tetrahydropyranyloxy)-3(S)-cyclohexyl-prop-trans-1-enyl]-7-anti-(2-tetrahydropyranyloxy)-cis-bicyclo[3,3,0]octane 6.7 g. of 2-oxa-3-oxo-6-syn-[3(S)-hydroxy-3(S)-cyclohexyl-prop-trans-1-enyl]-7-anti-hydroxy-cis-bicyclo[3,3,0]octane (prepared as described in Reference Example 4) were dissolved in 70 ml. of methylene chloride, and the mixture was reacted with 6.6 ml. of dihydropyran and 60 mg. of p-toluenesulphonic acid at 5° C. for 15 minutes to give 10.7 g. of the title compound as crystals having the following physical characteristics:

IR (KBr tablet); $\nu$: 2905, 2830, 1760, 1440, 1350, 1200, 1180, 1160, 1140, 1075, 1035, 1010, 975, 910, 890, 870 and 820 cm$^{-1}$;

NMR (CDCl$_3$ solution); $\delta$: 5.7 − 5.15 (2H, m), 5.15 − 4.8 (1H, m), 4.8 − 4.3 (2H, m), 4.2 − 3.1 (6H, m);

TLC (developing solvent benzene:ethyl acetate = 2:3); Rf = 0.75.

REFERENCE EXAMPLE 6

2-Oxa-3-hydroxy-6-syn-[3(S)-(2-tetrahydropyranyloxy)-3(S)-cyclohexyl-prop-trans-2-enyl]-7-anti-(2-tetrahydropyranyloxy)-cis-bicyclo[3,3,0]octane 10.7 g. of 2-oxa-3-oxo-6-syn-[3(S)-(2-tetrahydropyranyloxy)-3(S)-cyclohexyl-prop-trans-1-enyl]-7-anti-(2-tetrahydropyranyloxy)-cis-bicyclo[3,3,0]octane (prepared as described in Reference Example 5) were reduced at −60° C. for 5 minutes with 33 ml. of a solution of diisobutylaluminium hydride in toluene (25% w/v) to give 11 g. of the title compound as a waxy substance having the following physical characteristics:

IR (liquid film); $\nu$: 3400, 2950, 2850, 1440, 1350, 1200, 1130, 1080, 1040, 1025, 1010 and 980 cm$^{-1}$;

NMR (CDCl$_3$ solution); $\delta$: 5.8 − 5.15 (2H, m), 5.1 − 4.3 (3H, m), 4.3 − 3.1 (6H, m);

TLC (developing solvent benzene:ethyl acetate = 2:3); Rf = 0.53.

EXAMPLE 1

9α-Hydroxy-11α, 15(S)-bis-(2-tetrahydropyranyloxy)-15(S)-cyclohexyl-ω-pentanor-prosta-cis-5,trans-13-dienoic acid A solution of 31 g. of 4-carboxy-n-butyltriphenyl-phosphonium bromide in 80 ml. of dimethyl sulphoxide were mixed with 75 ml. of dimethyl sulphoxide containing 2M of sodiomethylsulphinylcarbanide (0.15 mole as sodiomethylsulphinylcarbanide) whilst maintaining the temperature at 25° C. The solution became scarlet about half way through the addition. A solution of 11 g. of 2-oxa-3-hydroxy-6-syn-[3(S)-(2tetrahydropyranyloxy)-3(S)-cyclohexyl-prop-trans-1-enyl]-7-anti-(2-tetrahydro-pyranyloxy)-cis-bicyclo[3,3,0]octane (prepared as described in Reference Example 6) in 70 ml. of dimethyl sulphoxide were added, and the mixture stirred vigorously at room temperature for 1 hour. The reaction mixture was poured into 1.2 liters of ice-water and neutral substance was removed by extraction with a mixture of ethyl acetate and diethyl ether (1:1). The aqueous layer was acidified to pH 2.0 with a saturated aqueous solution of oxalic acid and extracted with a mixture of diethyl ether and n-pentane (1:1). The extract, after washing with water, was dried over sodium sulphate and concentrated under reduced pressure. The residue was subjected to column chromatography on silica gel using benzene:ethanol (20:1) as eluent to give 8.9 g. of pure title compound as an oil having the following physical characteristics:

IR (liquid film); $\nu$: 3450, 3000, 2925, 2850, 2700–2300, 1710, 1445, 1350, 1265, 1205, 1190, 1140, 1125, 1080, 1030, 1010, 980, 915, 880 and 765 $cm^{-1}$;

NMR (CDCl$_3$ solution); $\delta$: 6.6 – 5.85 (2H, $m$), 5.7 – 4.9 (4H, $m$), 4.9 – 4.4 (2H, $m$), 4.35 – 3.15 (7H, $m$);

TLC (developing solvent benzene:ethyl acetate = 2:3); Rf = 0.20.

EXAMPLE 2

15(S)-Cyclohexyl-ω-pentanor-PGF$_2$ 700 mg. of 9α-hydroxy-11α,15(S)-bis-(2-tetrahydropyranyloxy)-15(S)-cyclohexyl-ω-pentanor-prosta-cis-5,trans-13-dienoic acid (prepared as described in Example 1) were dissolved in 22 ml. of a mixture of acetic acid, water and tetrahydrofuran (65:35:10), and the resulting solution was stirred vigorously at 38° to 40° C. for 2 hours. The reaction mixture was then poured into 100 ml. of ice-water and extracted with ethyl acetate. The extract was washed with water, dried over magnesium sulphate and concentrated under reduced pressure. The residue was subjected to column chromatography on silica gel using cyclohexane:ethyl acetate (1:1) as eluent, to obtain 165 mg. of the pure title compound as an oil having the following physical characteristics:

IR (liquid film); $\nu$: 3350, 3000, 2900, 2850, 2700–2300, 1710, 1450, 1410, 1380, 1240, 1200, 1100, 1050, 1005, 980 and 900 $cm^{-1}$;

NMR (CDCl$_3$ + acetone-d$_6$ solution); $\delta$: 5.65 – 5.0 (8H, $m$), 4.25 – 4.04 (1H, $m$), 4.04 – 3.65 (2H, $m$);

TLC (developing solvent chloroform:tetrahydrofuran:acetic acid = 10:2:1); Rf = 0.15;

Optical rotation: $[\alpha]_D^{24} = +23.6°$ ($c = 0.95$, ethanol).

EXAMPLE 3

9Oxo-11α,15(S)-bis-(2-tetrahydropyranyloxy)-15(S)-cyclohexyl-ω-pentanor-prosta-cis-5,trans-13-dienoic acid 1.93 g. of 9α-hydroxy-11α,15(S)-bis-(2-tetrahydropyranyloxy)-15(S)-cyclohexyl-ω-pentanor-prosta-cis-5,trans-13-dienoic acid (prepared as described in Example 1) were dissolved in 60 ml. of diethyl ether, and cooled to 0° to 5° C. Then, 45 ml. of a chromic acid solution (prepared by dissolving 3.2 g. of chromium trioxide, 10.8 g. of manganese sulphate and 3.56 ml. of sulphuric acid in water to make the total volume 80 ml.) were added to the solution. The reaction mixture was stirred vigorously at 0° to 5° C. for 40 minutes and diluted with diethyl ether to separate it into two layers. The aqueous layer was extracted with diethyl ether. The combined extracts were washed sufficiently with water until the washing was not coloured yellow, dried over sodium sulphate and then concentrated under reduced pressure. The residue was subjected to column chromatography on silica gel using benzene:ethanol (30:1) as eluent to give 1.60 g. of the title compound as an oil having the following physical characteristics:

IR (liquid film); $\nu$: 3500–3200, 3080, 3030, 2925, 2850, 2700–2300, 1740, 1710, 1440, 1350, 1260, 1240, 1205, 1185, 1160, 1135, 1080, 1060, 1045, 1005, 980, 910 and 875 $cm^{-1}$;

NMR (CDCl$_3$ solution; $\delta$: 10.53 (1H, $s$), 5.7 – 5.15 (4H, $m$), 4.85 – 4.45 (2H, $m$), 4.3 – 3.15 (6H, $m$);

TLC (developing solvent benzene:ethyl acetate = 2:3); Rf = 0.73.

EXAMPLE 4

15(S)-Cyclohexyl-ω-pentanor-PGE$_2$ 1.6 g. of 9-oxo-11α,15(S)-bis-(2-tetrahydropyranyloxy)-15(S)-cyclohexyl-ω-pentanor-prosta-cis-5,-trans-13-dienoic acid (prepared as described in Example 3) were dissolved in 44 ml. of a mixture of acetic acid, water and tetrahydrofuran (65:35:10) and stirred at 38° to 40° C. for 1 hour. The reaction mixture was then poured into 200 ml. of ice-water, extracted with ethyl acetate, washed with water, dried over sodium sulphate and concentrated under reduced pressure. The residue was subjected to column chromatography on silica gel using cyclohexane: ethyl acetate (1:1 to 4:1) as eluent to give 600 mg. of the title compound as an oil having the following physical characteristics:

IR (liquid film); $\nu$: 3350, 3000, 2900, 2850, 2700–2300, 1740, 1710, 1440, 1405, 1375, 1245, 1160, 1080, 1050, 1005 and 980 $cm^{-1}$; NMR (CDCl$_3$ solution); $\delta$: 5.82 (3H, broad $s$), 5.67 – 5.2 (4H, $m$), 4.2 – 3.7 (2H, $m$), 2.74 (1H, $q$);

TLC (developing solvent chloroform:tetrahydrofuran:acetic acid = 10:2:1); Rf = 0.24;

Optical rotation: $[\alpha]_D^{22} = -68.2°$ ($c = 0.85$, ethanol).

EXAMPLE 5

15(S)-Cyclohexyl-ω-pentanor-PGA$_2$ 250 mg. of 15(S)-cyclohexyl-ω-pentanor-PGE$_2$ (prepared as described in Example 4) were dissolved in 13 ml. of a mixture of tetrahydrofuran and 1N hydrochloric acid (1:1), and the solution was stirred at 60° C. for 3 hours with 118 mg. of cupric chloride dihydrate. The reaction mixture was then diluted with ethyl acetate, washed with water, dried over magnesium sulphate and concentrated under reduced pressure. The residue was subjected to column chromatography on silica gel using cyclohexane:ethyl acetate (3:1) as eluent to give 164 mg. of the title compound as an oil having the following physical characteristics:

IR (liquid film); $\nu$: 3400, 3000, 2915, 2850, 2700–2360, 1710, 1690, 1585, 1445, 1240, 1180, 1010 and 980 $cm^{-1}$;

NMR (CDCl$_3$ solution); $\delta$: 7.51 (1H, $q$), 6.19 (1H, $q$), 5.91 (4H, broad $s$), 5.68 – 5.3 (4H, $m$), 3.95 – 3.75 (1H, $m$), 3.35 – 3.15 (1H, $m$);

TLC (developing solvent chloroform:tetrahydrofuran: acetic acid = 10:2:1); Rf = 0.68;

Optical rotation: $[\alpha]_D^{22} = +177.4°$ ($c = 0.975$, ethanol); UV: $\lambda_{max} = 221$ m$\mu$ (in 50% ethanol).

EXAMPLE 6

9α-Hydroxy-11α,15(S)-bis-(2-tetrahydropyranyloxy)-15(S)-cyclohexyl-ω-pentanor-prost-trans-13-enoic acid 1.4 g. of 5% (w/w) palladium on charcoal were suspended in 80 ml. of methanol. Air in the apparatus was replaced by hydrogen and a solution of 2.5 g. of 9α-hydroxy-11α,15(S)-bis-(2-tetrahydropyranyloxy)-15(S)-cyclohexyl-ω-pentanor-prosta-cis-5,trans-13-dienoic acid (prepared as described in Example 1) in 50 ml. of methanol were added thereto. Catalytic reduction of the compound was carried out at room temperature under ambient pressure for about 40 minutes. After completion of the reaction, the catalyst was separated by filtration and the filtrate was evaporated to dryness under reduced pressure to give 2.13 g. of the title compound having the following physical characteristics:

IR (liquid film); $\nu$: 3430, 2930, 2845, 2700–2300, 1710, 1445, 1375, 1350, 1260, 1240, 1200, 1185, 1135, 1120, 1080, 1025 and 980 cm$^{-1}$;

NMR (CDCl$_3$ solution); δ: 6.57 (2H, s), 5.63 – 5.15 (2H, m), 4.8 – 4.45 (2H, m), 4.35 – 3.2 (7H, m);

TLC (developing solvent chloroform:tetrahydrofuran:acetic acid = 10:2:1); Rf = 0.73.

EXAMPLE 7

15(S)-Cyclohexyl-ω-pentanor-PGF$_1$ 470 mg. of 9α-hydroxy-11α,15(S)-bis-(2-tetrahydropyranyloxy)-15(S)-cyclohexyl-ω-pentanor-prost-trans-13-enoic acid (prepared as described in Example 6) were dissolved in 22 ml. of a mixture of acetic acid, water and tetrahydrofuran (65:35:10), and the resulting solution was stirred vigorously at 40° C. for 1.5 hours. The reaction mixture was then poured into 100 ml. of ice-water and extracted with ethyl acetate. The extract was washed with water, dried over magnesium sulphate, and concentrated under reduced pressure. The residue was purified by column chromatography on silica gel using chloroform:tetrahydrofuran (5:1), and then ethyl acetate along as eluents, to give white crystals. The crystals were recrystallized from ethyl acetate to give 154 mg. of the title compound having the following physical characteristics:

m.p. 115.5° to 118.5° C.;

IR (KBr tablet); $\nu$: 3420, 2900, 2850, 2700–2300, 1700, 1445, 1405, 1305, 1205, 1090, and 980 cm$^{-1}$;

NMR (CDCl$_3$ solution); δ: 5.38 – 5.2 (2H, m), 4.8 – 3.0 (7H, m);

TLC (developing solvent chloroform:tetrahydrofuran:acetic acid = 10:2:1); Rf = 0.15;

Optical rotation: $[\alpha]_D^{23} = +28.0°$ ($c = 0.775$, ethanol).

EXAMPLE 8

15(S)-Cyclohexyl-ω-pentanor-PGE$_1$ 1.65 g. of 9α-hydroxy-11α,15(S)-bis-(2-tetrahydropyranyloxy)-15(S)-cyclohexyl-ω-pentanor-prost-trans-13-enoic acid (prepared as described in Example 6) were dissolved in 50 ml. of diethyl ether. The solution was cooled to 0° to 5° C. and then 40 ml. of a chromic acid solution (prepared by dissolving 3.2 g. of chromium trioxide, 10.8 g. of manganese sulphate and 3.56 ml. of sulphuric acid in water to make the total volume 80 ml.) were added and the reaction mixture stirred vigorously at 0° to 5° C. for 40 minutes. The reaction mixture was diluted with diethyl ether to separate it into two layers. The aqueous layer was extracted with diethyl ether. The combined extracts were washed sufficiently with water until the washing was not coloured yellow, dried over sodium sulphate and then concentrated under reduced pressure to give 1.35 g. of 9-oxo-11α,15(S)-bis-(2-tetrahydropyranyloxy)-15(S)-cyclohexyl-ω-pentanor-prost-trans-13-enoic acid having the following physical characteristics:

IR (liquid film); $\nu$: 3500, 2920, 2845, 2700–2400, 1740, 1710, 1445, 1240, 1200, 1135, 1120, 1080, 1040, 1025 and 980 cm$^{-1}$;

NMR (CDCl$_3$ solution); δ: 10.28 (1H, s), 5.8 – 5.3 (2H, m), 4.85 – 4.45 (2H, m), 4.3 – 3.2 (6H, m);

TLC (developing solvent benzene:ethyl acetate = 2:3); Rf = 0.46.

1.35 g. of 9-oxo-11α,15(S)-bis-(2-tetrahydropyranyloxy)-15(S)-cyclohexyl-ω-pentanor-prost-trans-13-enoic acid (prepared as described above) were dissolved in 35 ml. of a mixture of acetic acid, water and tetrahydrofuran (65:35:10) and stirred at 38° to 40° C. for 1 hour. The reaction mixture was then poured into 150 ml. of ice-water, extracted with ethyl acetate, washed with water, dried over sodium sulphate and concentrated under reduced pressure. The residue was subjected to column chromatography on silica gel using chloroform:tetrahydrofuran (5:1), and then ethyl acetate alone as eluents and the product subsequently recrystallized from ethyl acetate to give 196 mg. of the title compound as white crystals having the following physical characteristics:

IR (KBr tablet); $\nu$: 3420, 3340, 2900, 2850, 2700–2300, 1745, 1715, 1400, 1345, 1285, 1220, 1170, 1075, 1000 and 980 cm$^{-1}$;

NMR CDCl$_3$ solution); δ: 5.9 – 5.25 (5H, m), 4.2 – 3.58 (2H, m), 2.75 (1H, d—d);

TLC (developing solvent chloroform:tetrahydrofuran:acetic acid = 10:2:1); Rf = 0.25;

Optical rotation: $[\alpha]_D^{23} = -64.1°$ ($c = 0.85$, ethanol).

REFERENCE EXAMPLE 7

Dimethyl 2-oxo-2-cyclobutylethylphosphonate

A solution of n-butyllithium was prepared from 10 g. of lithium, 97 g. of n-butyl bromide and 310 ml. of diethyl ether, and cooled to below −50° C. 70.5 g. of dimethyl methylphosphonate in 450 ml. of tetrahydrofuran were added to the solution under an atmosphere of nitrogen at −50° C. and stirred for 15 minutes at the same temperature.

To the solution, 29 g. of cyclobutanecarboxylic acid ethyl ester in 70 ml. of tetrahydrofuran were added dropwise keeping the temperature below −55° C. and stirred at the same temperature for 2 hours and then for 16 hours at 0° C. The reaction mixture was adjusted to pH 4 to 5 and concentrated. The residue was treated with diethyl ether, washed with water, dried and concentrated. The resultant product was subjected to distillation in vacuo, to give 22.7 g. of the title compound as an oil having the following physical characteristics:

b.p. 110° to 115° C./0.09 mm.Hg;

IR (liquid film); $\nu$: 2950, 1710, 1460, 1400 and 1350 cm$^{-1}$;

NMR (CDCl$_3$ solution); δ: 3.86 – 3.68 (6H, d), 3.7 – 3.2 (1H, m), 3.25 – 2.88 (2H, d).

REFERENCE EXAMPLE 8

2-Oxa-3-oxo-6-syn-(3-oxo-3-cyclobutyl-prop-trans-1-enyl)-7-anti-acetoxy-cis-bicyclo[3,3,0]octane Under an atmosphere of nitrogen, 180 g. of chromium trioxide were added to 292 ml. of pyridine and 3 liters of methylene chloride, stirred at room temperature for 15 minutes and allowed to cool to 0° to 5° C. 48.3 g. of 2-oxa-3-oxo-6-syn-hydroxymethyl-7-anti-acetoxy-cis-bicyclo[3,3,0]octane [prepared as described in J. Amer. Chem. Soc. 92, 397 (1970)] in 300 ml. of methylene chloride were then added. The reaction mixture was stirred at 0° to 5° C. for 15 minutes. The solution was filtered and the filtrate was concentrated at 0° C. under reduced pressure.

4.8 g. of sodium hydride (65.1% content) were suspended in 1.4 liters of tetrahydrofuran and stirred at room temperature under an atmosphere of nitrogen. To the solution there was added, dropwise, dimethyl 2-oxo-2-cyclobutylethylphosphonate (prepared as described in Reference Example 7) in 140 ml. of tetrahydrofuran and stirred for 30 minutes until evolution of hydrogen ceased. The aldehyde solution prepared as described above was added to the reaction mixture and stirred for 1 hour at room temperature. After completion of the reaction, the solution was acidified with acetic acid and filtered. The filtrate was concentrated. The residue was subjected to column chromatography on silica gel using methylene chloride as eluent to give 32 g. of the pure title compound having the following physical characteristics:

IR (liquid film); ν: 2950, 1780, 1740, 1670, 1630 and 1420 cm$^{-1}$;

NMR (CDCl$_3$ solution); δ: 7.1 – 5.9 (2H, m), 5.4 – 4.7 (2H, m), 4.0 – 3.2 (1H, m);

TLC (developing solvent methylene chloride:methanol = 19:1); Rf = 0.3.

REFERENCE EXAMPLE 9

2-Oxa-3-oxo-6-syn-(3-hydroxy-3-cyclobutyl-prop-trans-1-enyl)-7-anti-acetoxy-cis-bicyclo[3,3,0]octane 27 g. of 2-oxa-3-oxo-6-syn-(3-oxo-3-cyclobutyl-prop-trans-2-enyl)-7-anti-acetoxy-cis-bicyclo[3,3,0]octane (prepared as described in Reference Example 8) in 350 ml. of methanol were cooled to −35° to −40° C. and 10.5 g. of sodium borohydride were added. After stirring for 15 minutes the reaction mixture was neutralized with acetic acid and concentrated. The residue was mixed with water and ethyl acetate, extracted with ethyl acetate, washed, dried and concentrated to give 26 g. of the title compound having the following physical characteristics:

IR (liquid film); ν: 3450, 2950, 1780, 1750 and 1380 cm$^{-1}$;

NMR (CDCl$_3$ solution); δ: 5.6 – 5.3 (2H, m), 5.2 – 4.6 (2H, m), 4.2 – 3.5 (2H, m);

TLC (developing solvent methylene chloride:methanol = 19:1); Rf = 0.32.

REFERENCE EXAMPLE 10

2-Oxa-3-oxo-6-syn-(3-hydroxy-3-cyclobutyl-prop-trans-1-enyl)-7-anti-hydroxy-cis-bicyclo[3,3,0]octane 15 g. of 2-oxa-3-oxo-6-syn-(3-hydroxy-3-cyclobutyl-prop-trans-1-enyl)-7-anti-acetoxy-cis-bicyclo[3,3,0]octane (prepared as described in Reference Example 9), 6.2 g. of potassium carbonate and 200 ml. of methanol were mixed and stirred at room temperature for 15 minutes. The reaction mixture was adjusted to pH 5 with 1N hydrochloric acid and extracted with ethyl acetate. The extract was washed with aqueous sodium bicarbonate solution, dried and concentrated under reduced pressure, to give 10.5 g. of the title compound as an oil having the following physical characteristics:

IR (liquid film); ν: 3400, 2950 and 1760 cm$^{-1}$;

NMR (CDCl$_3$ solution); δ: 5.8 – 5.3 (2H, m), 5.1 – 4.7 (1H, m), 4.3 – 3.5 (4H, m), 3.5 – 3.1 (1H, m);

TLC (developing solvent methylene chloride:methanol = 19:1); Rf = 0.11.

REFERENCE EXAMPLE 11

2-Oxa-3-oxo-6-syn-[3-(2-tetrahydropyranyloxy)-3-cyclobutyl-prop-trans-1-enyl]-7-anti-(2-tetrahydropyranyloxy)-cis-bicyclo[3,3,0]octane 10.5 g. of 2-oxa-3-oxo-6-syn-(3-hydroxy-3-cyclobutyl-prop-trans-1-enyl)-7-anti-hydroxy-cis-bicyclo[3,3,0]octane (prepared as described in Reference Example 10) were dissolved in 200 ml. of methylene chloride and the mixture was reacted with 11 ml. of dihydropyran and 100 mg. of p-toluenesulphonic acid at room temperature for 15 minutes to give 19 g. of the title compound as an oil having the following physical characteristics:-

IR (liquid film); : 2930, 1780 cm$^{-1}$;

NMR (CDCl$_3$ solution); δ: 5.9 – 5.2 (2H, m), 5.2 – 4.75 (1H, m), 4.75 – 4.3 (2H, m) 4.3 – 3.2 (8H, m);

TLC (developing solvent methanol:methylene chloride = 1:19); Rf = 0.36.

REFERENCE EXAMPLE 12

2-Oxa-3-hydroxy-6-syn-[3-(2-tetrahydropyranyloxy)-3-cyclobutyl-prop-trans-1-enyl]-7-anti-(2-tetrahydropyranyloxy)-cis-bicyclo[3,3,0]octane 17.5 g. of 2-oxa-3-oxo-6-syn-[3-(2-tetrahydropyranyloxy)-3-cyclobutyl-prop-trans-1-enyl]-7-anti-(2-tetrahydropranyloxy)-cis-bicyclo[3,3,0]octane (prepared as described in Reference Example 11) were reduced at −60° C. for 15 minutes with 60 ml. of a solution of diisobutylaluminium hydride in toluene (25% w/v) to give 17.6 g. of the title compound as an oil having the following physical characteristics:-

IR (liquid film); : 3400, 2930 cm$^{-1}$;

NMR (CDCl$_3$ solution); δ: 5.8 – 5.1 (3H, m), 5.1 – 4.3 (3H, m), 4.25 – 3.0 (7H, m);

TLC (developing solvent methylene chloride:methanol = 19:1); Rf = 0.2.

EXAMPLE 9

9α-Hydroxy-11α,15-bis-(2-tetrahydropyranyloxy)-15-cyclobutyl-ω-pentanor-prosta-cis-5,trans-13-dienoic acid A solution of 132 g. of 4-carboxy-n-butyltriphenylphosphonium bromide in 220 ml. of dimethyl sulphoxide was mixed with 180 ml. of dimethyl sulphoxide containing 0.62 moles of sodiomethylsulphinylcarbanide whilst maintaining the temperature at 25° C. The solution became scarlet about half way through the addition. A solution of 17.6 of 2-oxa-3-hydroxy-6-syn-[3-(2-tetrahydropyranyloxy)-3-cyclobutyl-prop-trans-1-enyl]-7-anti-(2-tetrahydropyranyloxy)-cis-bicyclo[3,3,0]octane (prepared as described in Reference Example 12) in 100 ml. of dimethyl sulphoxide was added, and the mixture stirred vigorously at room temperature for 1.5 hours. The reaction mixture was poured into 2.5 liters of icewater containing potassium bicarbonate and neutral substance was removed by extraction with a mixture of ethyl acetate and diethyl ether (1:1). The aqueous layer was acidified to pH 2 with a saturated aqueous solution of oxalic acid and extracted with a mixture of diethyl ether and n-pentane (1:1). The extract, after washing with water, was dried over sodium sulphate and concentrated under reduced pressure to give 15 g. of the title compound having the following physical characteristics:-

IR (liquid film); : 3450, 2950 and 1740 cm$^{-1}$;

NMR (CDCl$_3$ solution); δ; 6.7 – 5.9 (2H, m), 5.8 – 5.0 (4H, m), 4.9 – 4.3 (2H, m), 4.3 – 3.0 (7H, m);

TLC (developing solvent methylene chloride:methanol = 19:1); Rf = 0.14.

EXAMPLE 10

15(S)-Cyclobutyl-ω-pentanor-PGF$_2$ and 15(R)-cyclobutyl-ω-pentanor-PGF$_2$ 2 g. of 9α-hydroxy-11α,15-bis-(2-tetrahydropyranayloxy)-15-cyclobutyl-ω-pentanor-prosta-cis-5,trans-13-dienoic acid (prepared as described in Example 9) were dissolved in a mixture of 20 ml. of tetrahydrofuran, 18 ml. of water and 2 ml. of hydrochloric acid and the resulting solution was stirred vigorously at 40° to 50° C. for 1.5 hours. The reaction mixture was then poured into 100 ml. of ice-water and extracted with ethyl acetate. The extract was washed with water, dried over magnesium sulphate and concentrated under reduced pressure. The residue was subjected to column chromatography on silica gel using tetrahydrofuran:chloroform (1:9) as eluent, to give 226 mg. of 15(S)-cyclobutyl-ω-pentanor-PGF$_2$ as crystals having the following physical characteristics:- m.p. 112° to 114° C.;

IR (liquid film); ν: 3400, 2950 and 1700 cm$^{-1}$;

NMR (CDCl$_3$ + dimethyl sulphoxide-d$_6$ solution); δ: 5.7 – 4.2 (8H, m), 4.2 – 3.6 (3H, m);

TLC (developing solvent tetrahydrofuran:chloroform:acetic acid = 2:10:1); Rf = 0.05, [15(S)].

In addition, 264 mg. of 15(R)-cyclobutyl-ω-pentanor-PGF$_2$ and 180 mg. of a mixture of the two title compounds were obtained. [The 15(R) epimer had the same IR and NMR values; TLC (developing solvent tetrahydrofuran:chloroform:acetic acid = 2:10:1); Rf = 0.11]

EXAMPLE 11

9-Oxo-11α,15-bis-(2-tetrahydropyranyloxy)-15-cyclobutyl-Ω-pentanor-prosta-cis-5,trans-13-dienoic acid 5 g. of 9α-hydroxy-11α,15-bis-(2-tetrahydropyranyloxy)-15-cyclobutyl-ω-pentanor-prosta-cis-5,trans-13-dienoic acid (prepared as described in Example 9) were dissolved in 400 ml. of diethyl ether and cooled to 5° C. Then, a chromic acid solution (prepared by dissolving 6.45 g. of chromiun trioxide, 30.7 g. of manganese sulphate and 7.2 ml. of sulphuric acid in 152.5 ml. of water) was added to the solution. The reaction solution was stirred vigorously at 5° C. for 3 hours and diluted with diethyl ether to separate it into two layers. The aqueous layer was extracted with diethyl ether. The combined extracts were washed sufficiently with water until the washing was not coloured yellow, dried over sodium sulphate and then concentrated under reduced pressure. The residue was subjected to column chromatography on silica gel using benzene:ethanol (20:1) as eluent to give 3.48 g. of the title compound as an oil having the following physical characteristics:-

IR (liquid film); ν: 3100, 2950, 1750 and 1710 cm$^{-1}$;

NMR (CDCl$_3$ solution); δ: 5.9 – 5.1 (4H, m), 5.0 – 4.5 (2H, m), 4.5 – 3.15 (8H, m);

TLC (developing solvent methylene chloride:methanol = 19:1), Rf = 0.2.

EXAMPLE 12

15(S)-Cyclobutyl-ω-pentanor-PGE$_2$ and 15(R)-cyclobutyl-ω-pentanor-PGE$_2$ 3.48 g. of 9-oxo-11α,15-bis-(2-tetrahydropyranyloxy)-15-cyclobutyl-ω-pentanor-prosta-cis-5,trans-13 dienoic acid (prepared as described in Example 11) were dissolved in 5 ml. of tetrahydrofuran, 32.5 ml. of acetic acid and 17.5 ml. of water and stirred at 40° C. for 2.5 hours. The reaction mixture was then poured into 200 ml. of icewater, extracted with ethyl acetate, washed with water, dried and concentrated under reduced pressure. The residue was subjected to column chromatography on silica gel using cyclohexane:ethyl acetate (1:1) as eluent to give 450 mg. of 15(S)-cyclobutyl-ω-pentanor-PGE$_2$ as crystals having the following physical characteristics:- m.p. 75° to 77° C.;

IR (KBr tablet); : 3450, 2950, 1740 and 1705 cm$^{-1}$; NMR (CDCl$_3$ solution); δ: 6.5 – 5.8 (3H, m), 5.8 – 5.15 (4H, m), 4.3 – 3.7 (2H, m);

TLC (developing solvent chloroform:tetrahydrofuran:acetic acid = 10:2:1); Rf = 0.1.

In addition, 670 mg. of 15(R)-cyclobutyl-ω-pentanor-PGE$_2$ [same IR and NMR values; TLC (developing solvent chloroform:tetrahydrofuran:acetic acid = 10:2:1); Rf = 0.16] and 290 mg. of a mixture of the two title compounds were obtained.

EXAMPLE 13

15(S)-Cyclobutyl-ω-pentanor-PGA$_2$ 248 mg. of 15(S)-cyclobutyl-ω-pentanor-PGE$_2$ (prepared as described in Example 12) were dissolved in 50 ml. of a mixture of tetrahydrofuran and 1N hydrochloric acid (1:1), and the solution was stirred at 60° C. for 3 hours with 126 mg. of cupric chloride dihydrate. The reaction mixture was then diluted with ethyl acetate, washed with water, dried and concentrated under reduced pressure. The residue was subjected to column chromatography on silica gel using cyclohexane: ethyl acetate (1:1) as eluent to give 142 mg. of the title compound as an oil having the following physical characteristics:-

IR (liquid film); ν: 3400, 2950, 1700 and 1590 cm$^{-1}$;

NMR (CDCl$_3$ solution); δ: 7.6 – 7.4 (1H, dd), 6.7 – 6.3 (2H, m), 6.3 – 6.1 (4H, dd), 5.7 – 5.2 (4H, m), 4.2 – 3.9 (1H, m), 3.3 – 3.1 (1H, m);

TLC (developing solvent chloroform:tetrahydrofuran: acetic acid = 10:2:1); Rf = 0.28.

EXAMPLE 14

9α-Hydroxy-11α,15-bis-(2-tetrahydropyranyloxy)-15-cyclobutyl-ω-pentanor-prost-trans-13-enoic acid 1.5 g. of 5% (w/w) palladium on charcoal were suspended in 25 ml. of methanol. Air in the apparatus was replaced by hydrogen and a solution of 7.59 g. of 9α-hydroxy-11α,15-bis-(2-tetrahydropyranyloxy)-15- cyclobutyl-ω-pentanor-prosta-cis-5,trans-13 dienoic acid (prepared as described in Example 9) in 30 ml. of methanol were added thereto. Catalytic reduction of the compound was carried out at room temperature under ambient pressure for about 2 hours. After completion of the reaction, the catalyst was separated by filtration and the filtrate was evaporated to dryness under reduced pressure to give 6.8 g. of the title compound having the following physical characteristics:-

IR (liquid film); ν: 3450, 2950, 1710 cm$^{-1}$;

NMR (CDCl$_3$ solution); δ: 6.0 (2H, broad s), 5.8 - 5.1 (2H, m), 5.1 - 4.5 (2H, m);

TLC (developing solvent methylene chloride:methanol = 19:1); Rf = 0.18.

EXAMPLE 15

9-Oxo-11α,15-bis-(2-tetrahydropyranyloxy)-15-cyclobutyl-ω-pentanor-prost-trans-13-enoic acid 2.14 g. of 9α-hydroxy-11α,15-bis-(2-tetrahydropyranyloxy)-15-cyclobutyl-ω-pentanor-prost-trans-13-enoic acid (prepared as described in Example 14) were dissolved in 150 ml. of diethyl ether. The solution was cooled to 0° to 5° C. and then a mixture of 3.2 g. of chromium trioxide, 15 g. of manganese sulphate, 3.5 ml. of sulphuric acid and 75 ml. of water were added and the reaction mixture stirred vigorously at the same temperature for 1.5 hours. The reaction mixture was diluted with diethyl ether to separate it into two layers. The aqueous layer was extracted with diethyl ether. The combined extracts were washed sufficiently with water until the washing was not coloured yellow, dried over magnesium sulphate and then concentrated under reduced pressure. The residue was purified by column chromatography on silica gel using benzene:ethanol (20:1) as eluent to give 1.88 g. of the title compound as an oil having the following physical characteristics:-

IR (liquid film); : 3200, 2950, 1750 and 1710 cm$^{-1}$;

NMR (CDCl$_3$ solution); δ: 9.1 - 8.6 (1H, broad s), 5.8 - 5.1 (2H, m), 5.0 - 4.4 (2H, m), 4.4 - 3.2 (6H, m);

TLC (developing solvent methylene chloride:methanol = 19:1); Rf = 0.16.

EXAMPLE 16

15(S(-Cyclobutyl-ω-pentanor-PGE$_1$ and 15(R)-cyclobutyl-ω-pentanor-PGE$_1$ 1.8 g. of 9-oxo-11α,15-bis-(2-tetrahydropyranyloxy)-15-cyclobutyl-ω-pentanor-prost-trans-13-enoic acid (prepared as described in Example 15) were dissolved in a mixture of 3 ml. of tetrahydrofuran, 19.5 ml. of acetic acid and 10.5 ml. of water and stirred at 50° C. for 1 hour. The reaction mixture was then poured into 200 ml. of ice-water, extracted with ethyl acetate, washed with water, dried over magnesium sulphate and concentrated under reduced pressure. The residue was subjected to column chromatography on silica gel using cyclohexane:ethyl acetate (1:1) as eluent, to give 234 mg. of 15(S)-cyclobutyl-ω-pentanor-PGE$_1$ having the following physical characteristics:-

IR (liquid film); ν: 3400, 2950, 1750 and 1710 cm$^{-1}$;

NMR (CDCl$_3$ solution); δ: 6.4 - 5.1 (5H, m), 4.3 - 3.8 (2H, m);

TLC (developing solvent chloroform:tetrahydrofuran: acetic acid = 10:2:1); Rf = 0.1.

In addition, 278 mg. of 15(R)-cyclobutyl-ω-pentanor-PGE$_1$ [same IR and NMR values; TLC (developing solvent chloroform:tetrahydrofuran:acetic acid = 10:2:1); Rf = 0.16] and 177 mg. of a mixture of the two title compounds were obtained.

REFERENCE EXAMPLE 13

Dimethyl 2-oxo-2-cyclopentylethylphosphonate

A solution of n-butyllithium was prepared form 17 g. of lithium, 165 g. of n-butyl bromide and 880 ml. of diethyl ether, and cooled to below −55° C. 120 g. of dimethyl methylphosphonate in 950 ml. of tetrahydrofuran were added to the solution under an atmosphere of nitrogen at −60° C. and stirred for 15 minutes at that temperature.

To the solution thus obtained, 77 g. of cyclopentanecarboxylic acid ethyl ester in 480 ml. of tetrahydrofuran were added dropwise keeping the temperature below −55° C. and the mixture stirred at −60° to −70° C. for 2 hours and at 0° C. for 16 hours. The reaction mixture was then adjusted to pH 4 to 5 with acetic acid and concentrated under reduced pressure. The residue was treated with 2.5 liters of diethyl ether, washed with water, dried over magnesium sulphate and concentrated under reduced pressure. The residue was subjected to distillation in vacuo to give 53 g. of the title compound having the following physical characteristics:- b.p. 110° to 116° C./0.1 mm.Hg;

IR (liquid film); : 2930, 2850, 1710, 1445, 1320, 1260, 1180, 1060, 1035, 1010, 900 cm$^{-1}$;

NMR (CCl$_4$ solution); δ: 3.75 (6H, d), 3.20 (2H, d), 3.0 - 2.2 (1H, m).

REFERENCE EXAMPLE 14

2-Oxa-3-oxo-6-syn-(3-oxo-3-cyclopentyl-prop-trans-1-enyl)-7-anti-acetoxy-cis-bicyclo[3,3,0]octane Under an atmosphere of nitrogen, 117 g. of chromium trioxide were added to a mixture of 190 ml. of pyridine and 2.4 litres of methylene chloride, and the mixture stirred at room temperature for 15 minutes and then allowed to cool to −2° to −3° C. 41 g. of 2-oxa-3-oxo-6syn-hydroxymethyl-7-anti-acetoxy-cis-bicyclo[3,3,0]-octane [prepared as described in J. Amer. Chem. Soc. 92, 397, (1970)] in 170 ml. of methylene chloride were then added. The reaction mixture was stirred at −2° to −3° C. for 10 minutes. The solution was then filtered and the filtrate was concentrated under reduced pressure below 0° C.

5.0 g. of sodium hydride (65.1% content) were dissolved in 960 ml. of tetrahydrofuran and stirred at room temperature under an atmosphere of nitrogen. To the solution was added dropwise 35.8 g. of dimethyl 2-oxo-2-cyclopentylethylphosphonate (prepared as described in Reference Example 13) in 160 ml. of tetrahydrofuran and stirred for 20 minutes until evolution of hydrogen ceased. The aldehyde solution, prepared as described above, was added to the reaction mixture and stirred for 1 hour at room temperature. After completion of the reaction, the solution was acidified with acetic acid and filtered. The filtrate was concentrated. The residue was subjected to column chromatography on silica gel using benzene:ethyl acetate (4:1 to 2:1) as eluent to give 25 g. of the title compound having the following physical characteristics:-

IR (liquid film); ν: 3020, 2950, 2850, 1780, 1740, 1690, 1670, 1630, 1445, 1420, 1380, 1325, 1240, 1180, 975 cm$^{-1}$;

NMR (CDCl$_3$ solution); δ: 6.82 (1H, d—d), 6.35 (1H, d), 5.4 - 4.9 (2H, m), 2.02 (3H, s);

TLC (developing solvent benzene:ethyl acetate = 4:1); Rf = 0.33.

REFERENCE EXAMPLE 15

2-Oxa-3-oxo-6syn-[3(S)-hydroxy-3(S)-cyclopentyl-proptrans-1-enyl]-7-anti-acetoxy-cis-bicyclo[3,3,0]octane 25 g. of 2-oxa-3-6-syn-(3-oxo-3-cyclopentyl-prop-trans-1-enyl)-7-anti-acetoxy-cisbicyclo[3,3,9]octane (prepared as described in Reference Example 14) in 330 ml. of a mixture of methanol and tetrahydrofuran (1:1) were cooled to −40° to −45° C., and 9 g. of sodium borohydride were then added. After stirring for 5 minutes, the reaction mixture was neutralized with oxalic acid at −30° C. and allowed to warm to room temperature and then concentrated under reduced pressure. The residue was mixed with water and ethyl acetate, extracted with ethyl acetate and the organic extracts were washed with water, dried over magnesium sulphate and concentrated under reduced pressure. The residue was subjected to column chromatography on silica gel using diethyl ether-nhexane:ethyl acetate (5:3:2) as eluent to give 6.1 g. of the title compound, 5.2 g. of the corresponding 3(R)-compound and 3.0 g. of a mixture of them. The title compound has the following physical characteristics:-
IR (liquid film); $v$: 3450, 2950, 1775, 1740, 1380, 1255, 1180, 1080, 980 cm$^{-1}$;
NMR (CDCl$_3$ solution); $\delta$: 6.56 − 5.22 (2H, $m$), 5.20 − 4.55 (2H, $m$), 3.96 − 3.52 (1H, $m$), 2.03 (3H, $s$);
TLC (developing solvent benzene:ethyl acetate = 2:3); Rf = 0.56.

REFERENCE EXAMPLE 16

2-Oxa-3-oxo-6-syn-[3(S)-cyclopentyl-proptrans-1-enyl]-7-anti-hydroxy-cis-bicyclo[3,3,0]octane 6.0 g. of 2-oxa-3-oxo-6-syn-[3(S)-hydroxy-3(S)-cyclopentyl-prop-trans-1-enyl]-7-anti-acetoxy-cisbicyclo[3,3,0]octane (prepared as described in Reference Example 15), 2.4 g. of potassium carbonate and 75 ml. of methanol were mixed and stirred at room temperature for 10 minutes. The reaction mixture was adjusted to pH 3 with 2N hydrochloric acid, 400 ml. of water were added and the solution extracted with ethyl acetate. The extracts were washed with an aqueous sodium bicarbonate solution, dried over magnesium sulphate and concentrated under reduced pressure to give 4.7 g. of the title compound having the following physical characteristics:-
IR (liquid film); $v$: 3450, 2930, 2850, 1770, 1335, 1180, 1160, 1080, 1040, 1010, 980 cm$^{-1}$;
NMR (CDCl$_3$ solution); $\delta$: 5.72 − 5.27 (2H, $m$), 5.10 − 4.62 (1H, $m$);
TLC (developing solvent benzene:ethyl acetate = 2:3); Rf = 0.29.

REFERENCE EXAMPLE 17

2-Oxa-3-oxo-6-syn-[3(S)-(2-tetrahydropyranyloxy)-3(S)-cyclopentyl-prop-trans-1-enyl]-7-anti-(2-tetrahydropyranyloxy)-cis-bicyclo[3,3,0]octane 4.7 g. of 2-oxa-3-oxo-6-syn-[3(S)-hydroxy3(S)-cyclopentyl-prop-trans-1-enyl]-7-anti-hydroxy-cisbicyclo[3,3,0]octane (prepared as described in Reference Example 16) were dissolved in 50 ml. of methylene chloride and the mixture was reacted with 4.6 ml. of dihydropyran and 42 mg. of p-toluenesulphonic acid at 5° C. for 15 minutes to give 7.5 g. of the title compound having the following physical characteristics:-
IR (liquid film); $v$: 2950, 2830, 1770, 1440, 1350, 1200, 1180, 1160, 1140, 1075, 1040, 1010, 975 cm$^{-1}$;
NMR (CDCl$_3$ solution); $\delta$: 5.70 − 5.15 (2H, $m$), 5.15 − 4.82 (1H, $m$), 4.80 − 4.32 (2H, $m$), 4.23 − 3.10 (6H, $m$);
TLC (developing solvent benzene:ethyl = 2:3); Rf = 0.75.

REFERENCE EXAMPLE 18

2-Oxa-3-hydroxy-6-syn-[3(S)-(2-tetrahydropyranyloxy)-3(S)-cyclopentyl-prop-trans-1-enyl]-7-anti-(2-tetrahydropyranyloxy)-cis-bicyclo[3,3,0]octane 7.5 g. of 2-oxa-3-oxo-6-syn-[3(S)-(2-tetrahydropyranyloxy)-3(S)-cyclopentyl-prop-trans-1-enyl]-7-anti-(2-tetrahydropyranyloxy)-cis-bicyclo[3,3,0]octane (prepared as described in Reference Example 17) were reduced at −60° C. for 5 minutes with 23 ml. of a solution of diisobutylaluminium hydride in toluene (25% w/v) to give 7.5 g. of the title compound having the following physical characteristics:-
IR (liquid film); $v$: 3400, 2950, 2850, 1440, 1350, 1200, 1130, 1080, 1040, 1025, 1010, 980 cm$^{-1}$;
NMR (CDCl$_3$ solution); $\delta$: 5.78 − 5.15 (2H, $m$), 5.10 − 4.32 (3H, $m$), 4.38 − 3.10 (6H, $m$);
TLC (developing solvent benzene-ethyl acetate = 2:3); Rf = 0.54.

EXAMPLE 17

9α-Hydroxy-11α,15(S)-bis-(2-tetrahydropyranyloxy)-15(S)-cyclopentyl-ω-pentanor-prosta-cis-5,trans-13-dienoic acid A solution of 22 g. of 4-carboxy-n-butyltriphenylphosphonium bromide in 55 ml. of dimethyl sulphoxide was mixed with 53 ml. of dimethyl sulphoxide containing 2 moles of sodiomethylsulphinylcarbanide (105 mmole as sodiomethylsulphinylcarbanide) whilst maintaining the temperature at 25° C. Then a solution of 7.5 g. of 2-oxa-3-hydroxy-6-syn-[3(S)-(2-tetrahydropyranyloxy)-3(S)-cyclopentyl-prop-trans-1-enyl]-7-anti(2-tetrahydropyranyloxy)-cis-bicyclo[3,3,0]octane (prepared as described in Reference Example 18) in 50 ml. of dimethyl sulphoxide was added and the mixture was stirred vigorously at room temperature for one hour. The reaction mixture was poured into 900 ml. of ice-water and neutral substance was removed by extraction with a mixture of ethyl acetate and diethyl ether (1:1). The aqueous layer was acidified to pH 2.0 with a saturated aqueous oxalic acid solution and extracted with a mixture of diethyl ether and n-pentane (1:1). The extracts were washed with water, dried over sodium sulphate and concentrated under reduced pressure. The residue was subjected to column chromatography on silica gel using benzene:ethanol (20:1) as eluent to give 6.0 g. of the title compound having the following physical characteristics:-
IR (liquid film); $v$: 3400, 3000, 2930, 2850, 2700–2300, 1710, 1445, 1350, 1205, 1190, 1140, 1125, 1080, 1030, 980 cm$^{-1}$;
NMR (CDCl$_3$ solution); $\delta$: 6.62 − 5.85 (2H, $m$), 5.70 − 4.91 (4H, $m$), 4.91 − 4.38 (2H, $m$), 4.32 − 3.15 (7H, $m$);
TLC (developing solvent benzene:ethyl acetate = 2:3); Rf = 0.22.

EXAMPLE 18

15(S)-Cyclopentyl-ω-pentanor-prostaglandin-F$_2$ 300 mg. of 9α-hydroxy-11α,15(S)-bis-(2-tetrahydropyranyloxy)-15(S)-cyclopentyl-ω-pentanor-prosta-cis-5,trans-13-dienoic acid (prepared as described in Example 17) were dissolved in a mixture of 0.25 ml. of hydrochloric acid, 2.15 ml. of water and 4 ml. of tetrahydrofuran and the mixture was stirred vigorously at 40° to 42° C. for 40 minutes. The reaction mixture was then poured into 100 ml. of ice-water and extracted with ethyl acetate. The extracts were washed with water, dried over magnesium sulphate and concentrated under reduced pressure. The residue was subjected to column chromatography on silica gel using cyclohexane:ethyl acetate (1:1) as eluent to give 85 mg. of the pure title compound having the following physical characteristics:- m.p. 97° to 98° C.;
IR (KBr tablet); ν: 3260, 2900, 2850, 1700, 1410, 1340, 1190 cm$^{-1}$;
NMR (CDCl$_3$ + CD$_3$OD solution); δ: 5.7 – 5.1 (4H, m), 4.72 – 4.15 (4H, broad s), 4.25 – 4.00 (1H, m), 4.00 – 3.60 (2H, m);
TLC (developing solvent chloroform:tetrahydrofuran: acetic acid = 10:2:1); Rf = 0.16.

EXAMPLE 19

9-Oxo-11α,15(S)-bis-(2-tetrahydropyranyloxy)-15(S)-cyclopentyl-ω-pentanor-prosta-cis-5,trans-13-dienoic acid 570 mg. of 9α-hydroxy-11α,15(S)-bis-(2-tetrahydropyranyloxy)-15(S)-cyclopentyl-ω-pentanor-prosta-cis-5,trans-13 dienoic acid (prepared as described in Example 17) were dissolved in 7.8 ml. of diethyl ether and cooled to 0° to 5° C. Then a chromic acid solution (prepared from 1.33 g. of manganese sulphate, 284 mg. of chromium trioxide, 0.316 ml. of sulphuric acid and 7.0 ml. of water) was added to the solution and the reaction mixture was stirred vigorously at 0° C. for one hour. 0.2 ml. of isopropyl alcohol was added to the reaction mixture to quench the reaction and the mixture was separated into two layers. The aqueous layer was extracted with ethyl acetate. The combined extracts were washed sufficiently with water and an aqueous sodium chloride solution, dried over magnesium sulphate and concentrated under reduced pressure. The residue was subjected to column chromatography on silica gel using benzene-ethanol (20:1) as eluent to give 400 mg. of the title compound having the following physical characteristics:-

NMR (CDCl$_3$ solution); δ: 8.90 (1H, broad s), 5.9 – 5.1 (4H, m), 5.0 – 4.5 (2H, m), 4.5 – 3.2 ( H, m);
TLC (developing solvent methylene chloride:methanol = 20:1); Rf = 0.33.

EXAMPLE 20

15(S)-Cyclopentyl-ω-pentanor-prostaglandin-E$_2$ 400 mg. of 9-oxo-11α,15(S)-bis-(2-tetrahydropyranyloxy)-15(S)-cyclopentyl-ω-pentanor-prosta-cis-5,trans-13-dienoic acid (prepared as described in Example 19) were dissolved in a mixture of 3.85 ml. of acetic acid. 2.08 ml. of water and 1.4 ml. of tetrahydrofuran and stirred at 40° C. for 3 hours. The reaction mixture was then pured into ice-water and extracted with ethyl acetate. The extracts were washed with water and an aqueous sodium chloride solution, dried over magnesium sulphate and concentrated under reduced pressure. The residue was subjected to column chromatography on silica gel using cyclohexane:ethyl acetate (3:1 to 1:2) as eluent to give 140 mg. of the title compound as an oil having the following physical characteristics:-

IR (liquid film); ν: 3400, 2950, 2850, 1740, 1720, 1250, 1160, 1080, 980 cm$^{-1}$;
NMR (CDCl$_3$ solution); δ: 6.4 – 5.75 (3H, m), 5.75 – 5.5 (2H, m), 5.5 – 5.2 (2H, m), 4.3 – 3.6 (2H, m);
TLC (developing solvent chloroform:tetrahydrofuran; acetic acid = 10:2:1); Rf = 0.35.

EXAMPLE 21

9α-Hydroxy-11α,15(S)-bis-(2-tetrahydropyranyloxy)-15(S)-cyclopentyl-ω-pentanor-prost-trans-13-enoic acid 300 mg. of 5% (w/w) palladium on charcoal were suspended in 20 ml. of methanol. Air in the aparatus was replaced by hydrogen and a solution of 590 mg. of 9α-hydroxy-11α,15(S)-bis-(2-tetrahydropyranyloxy)-15(S)-cyclopentyl-ω-pentanor-prosta-cis-5,trans-13-dienoic acid (prepared as described in Example 17) in 7.6 ml. of methanol was added thereto. Catalytic reduction was carried out at room temperature under ambient pressure for 30 minutes. The catalyst was separated by filtration and the filtrate was evaporated to dryness under reduced pressure to give 503 mg. of the title compound having the following physical characteristic:-

NMR (CDCl$_3$ solution); δ: 5.7 – 5.0 (4H, m), 4.8 – 4.4 (2H, m), 4.3 – 3.2 (7H, m).

EXAMPLE 22

15(S)-Cyclopentyl-ω-pentanor-prostaglandin-E$_1$ 503 mg. of 9α-hydroxy-11α,15(S)-bis-(2-tetrahydropyranyloxy)-15(S)-cyclopentyl-ω-pentanor-prosta-trans-13-enoic acid (prepared as described in Example 21) were dissolved in 7 ml. of diethyl ether. The solution was cooled to 0° C. and then a chromic acid solution (prepared from 1.27 g. of manganese sulphate, 250 mg. of chromium trioxide, 0.278 ml. of sulphuric acid and 6.15 ml. of water) was added and the reaction mixture was stirred vigorously at 0° C. for 1 hour. Then 0.2 ml. of isopropyl alcohol was added to the reaction mixture to quench the reaction and the mixture was separated into two layers. The aqueous layer was extracted with ethyl acetate. The combined extracts were washed with water sufficiently, dried over magnesium sulphate and concentrated under reduced pressure to give 500 mg. of crude 9-oxo-11α,15(S)-bis-(2-tetrahydropyranyloxy)-15(S)-cyclopentyl-ω-pentanorprost-trans-13-enoic acid having the following physical characteristic:-

TLC (developing solvent methylene chloride:methanol = 20:1); Rf = 0.35.

The crude 9-oxo compound, thus obtained, was dissolved in a mixture of 4.8 ml. of acetic acid, 3.5 ml. of water and 1.7 ml. of tetrahydrofuran and stirred at 45° C. for 2 hours. The reaction mixture was diluted with water and extracted with ethyl acetate. The organic extracts were washed with water, dried over magnesium sulphate and concentrated under reduced pressure. The residue was subjected to column chromatography on silica gel using cyclohexane:ethyl acetate (3:1 to 1:2) as eluent to give 121 mg. of the title compound as white crystals having the following physical characteristics:-
m.p. 78° to 79° C.;
IR (KBr tablet); $\nu$: 3400, 2900, 2850, 1740, 1720, 1450, 1380, 1250, 980 cm$^{-1}$;
NMR (CDCl$_3$ solution); $\delta$: 5.9 – 5.4 (2H, m), 5.2 – 4.4 (3H, broad s), 4.25 – 3.75 (2H, m);
TLC (developing solvent chloroform:tetrahydrofuran: acetic acid = 10:2:1); Rf = 0.30.

REFERENCE EXAMPLE 19

2-Oxa-3-oxo-6-syn-(2-methoxycarbonyl-eth-trans-1-enyl)-7-anti-acetoxy-cis-bicyclo[3,3,0]octane Under an atmosphere of nitrogen and at laboratory temperature, 140 ml. of absolute methylene chloride and 16.1 ml. of absolute pyridine were stirred with 10 g. of chromium trioxide for 30 minutes. 20 g. of infusorial earth were then added to the solution. After cooling the temperature to 0° C., 2.14 g. of 2-oxa-3-oxo-6-syn-hydroxymethyl-7-anti-acetoxy-cisbicyclo[3,3,-0]octane [prepared as described in J. Amer. Chem. Soc. 92, 397 (1970)] in 20 ml. of methylene chloride were then added and the mixture stirred for 15 minutes at 0° C. The reaction mixture was then treated with 25 g. of sodium bisulphate and stirred for a further 10 minutes at 0° C. and filtered through a pad of magnesium sulphate. The filtrate was then concentrated under reduced pressure and below 0° C. to give 2-oxa-3-oxo-6-syn-formyl-7-anti-acetoxy-cis-bicyclo[3,3,-0]octane.

369 mg. of sodium hydride (65% content) were suspended in 60 ml. of absolute tetrahydrofuran. With stirring under an atmosphere of nitrogen at room temperature, 1.82 g. of trimethyl phosphonoacetate [prepared as described in Acad. Sci. Paris, Ser. A,B 262B, 515 (1966) were added to the suspension, and stirred for 30 minutes.

The formyl compound, obtained above, in 30 ml. of tetrahydrofuran, was added, whilst maintaining the temperature below 15° C., and stirred for 2 hours at 15° C. Then the reaction mixture was treated with 2 ml. of acetic acid to PH 5 and concentrated slightly. The product was treated with 20 ml. of water and extracted twice with 80 ml. of ethyl acetate (total volume 160 ml.). The organic layer was washed with an aqueous sodium chloride solution, dried over magnesium sulphate and concentrated under reduced pressure. The residue was purified by column chromatography on silica gel using a mixture of ethyl acetate:benzene (1:4) as eluent to give 2.0 g. of the tile compound having the following physical characteristics:- IR (liquid film); $\nu$: 2970, 1775, 1735, 1710, 1650, 1240, 1160, 1037 and 980 cm$^{-1}$;
NMR (CDCl$_3$ solution); $\delta$: 6.77 (1H, d), 5.87 (1H, d), 5.00 (2H, m), 3.70 (3H, s), 3.0 – 1.9 (6H, m), 2.04 (3H, s);
TLC (developing solvent ethyl acetate:benzene = 1:2); Rf = 0.38.

REFERENCE EXAMPLE 20

2-Oxa-3-oxo-6-syn:(2-methoxycarbonyl-eth-trans-1-enyl)-7-anti-hydroxy-cis-bicyclo[3,3,0]octane 2.68 g. of 2-oxa-3-oxo-6-syn-(2-methoxycarbonyleth-trans-1-enyl)-7-anti-acetoxy-cis-bicyclo[3,3,-0]octane (prepared as described in Reference Example 19) in 30ml. of absolute methanol and 1.38 g. of potassium carbonate were stirred at room temperature for 15 minutes, successively cooled in an ice-bath and neutralized with 20 ml. of 1N hydrochloric acid. 260 ml. of ethyl acetate and 27 ml. of an aqueous sodium bicarbonate solution were added to the reaction mixture which separated into two layers. The organic layer was washed with an aqueous sodium chloride solution, dried over magnesium sulphate and concentrated under reduced pressure to give 1.96 g. of the title compound having the following physical characteristics:-
IR (liquid film); $\nu$: 3430, 1786-1690 (broad) and 1650 cm$^{-1}$;
NMR (CDCl$_3$ solution); $\delta$: 6.82 (1H, dd), 5.90 (1H, d), 4.95 (1H, m), 3.72 (3H, s), 4.30 — 3.25 (2H, m), and 2.90 — 1.70 (6H, m);
TLC (developing solvent methylene chloride:methanol = 19.1); Rf = 0.38.

REFERENCE EXAMPLE 21

2Oxa-3-oxo-6-syn-(2-methoxycarbonyl-eth-trans-1-enyl)-7-anti-(2-tetrahydropyranyloxy)-cis-bicyclo[3,3,0]octane 2.31 g. of 2-oxa-3-oxo-6-syn-(2-methoxycarbonyl-eth-trans-1-enyl)-7-anti-hydroxy-cis-bicyclo[3,3,0]octane (prepared as described in Reference Example 20) were dissolved in 30 ml. of methylene chloride and stirred with 20 mg. of p-toluenesulphonic acid and 3 ml. of dihydropyran for 15 minutes at room temperature. The reaction mixture was neutralized with an aqueous sodium bicarbonate solution, diluted with ethyl acetate, washed with an aqueous sodium chloride solution, dried over magnesium sulphate and concentrated under reduced pressure. The residue was purified by column chromatography on silica gel using a mixture of ethyl acetate:benzene (1:3) as eluent to give 3.0 g. of the title compound as white crystals having the following physical characteristics:-
m.p. 85° C.;
IR (KBr tablet); $\nu$: 2930, 1770, 1710, 1650, 1343, 1240 and 1142 cm$^{-1}$;
NMR (CDCl$_3$ solution; $\delta$: 6.78 (1H, dd), 5.84 (1H, d), 4.97 (1H, m), 4.63 (1H, m), 3.71 (3H, s) and 4.30 — 3.20 (3H, m);
TLC (developing solvent, ethyl acetate:benzene = 1:2); Rf = 0.34.

REFERENCE EXAMPLE 22

2-Oxa-3-hydroxy-6-syn-(3-hydroxy-prop-trans-1-enyl):7-anti-(2-tetrahydropyranyloxy)-cis-bicyclo[3,3,0]octane 3.10 g. of 2-oxa-3-oxo-6-syn-(2-methoxycarbonyl-eth-trans-1-enyl)-7-anti-(2-tetrahydropyranyloxy)-cis-bicyclo[3,3,0]octane (prepared as described in Reference Example 21) were dissolved in 100 ml. of toluene and cooled to −65° C. To the solution, 23 ml. of a solution of diisobutylaluminium hydride in toluene (25% w/v) were added and stirred for 20 minutes at −60° C. Methanol was then added to decompose excess diisobutylaluminium hydride together with water. The precipitate was filtered off and the filtrate was dried and concentrated under reduced pressure to give 2.8 g. of the title compound having the following physical characteristics:
IR (liquid film); $\nu$: 3390, 2930, 1350 and 1120 cm$^{-1}$;
NMR (CDCl$_3$ solution); $\delta$: 5.75 – 5.15 (3H, m), and 4.75 – 3.34 (8H, m);
TLC (developing solvent methylene chloride:methanol = 19:1); Rf = 0.23.

REFERENCE EXAMPLE 23

2α-(6-Methoxycarbonyl-hex-cis-2-enyl)-3β-(3-hydroxyprop-trans-1-enyl)-4α-(2-tetrahydropyranyloxy)-cyclopentan-1α-ol 2.94 g. of sodium hydride (65% content) were suspended in 40 ml. of dimethyl sulphoxide and stirred with heating at 65° C. for 40 minutes to obtain sodiomethylsulphinylcarbanide. The reaction mixture was allowed to cool to room temperature and then added dropwise to a solution of 18.5 g. of 4-carboxy-n-butyltriphenylphosphonium bromide in 40 ml. of dimethyl sulphoxide, the reaction temperature being kept within the range of 20° to 25° C.

A solution of 2.84 g. of 2-oxa-3-hydroxy-6-syn-(3-hydroxy-prop-trans-1-enyl)-7-anti-(2-tetrahydropyranyloxy)-cis-bicyclo[3,3,0]octane (prepared as described in Reference Example 22) in 40 ml. of dimethyl sulphoxide was added, and the mixture stirred vigorously at 25° C. for 1 hour. The reaction mixture was poured into 500 ml. of ice-water and neutral substances were removed by extraction with a mixture of ethyl acetate and diethyl ether (1:1). The aqueous layer was acidified to pH 3 with a saturated oxalic acid solution and extracted with a mixture of diethyl ether and ethyl acetate (1:1). The extracts, after washing with water, were dried over magnesium sulphate and concentrated under reduced pressure to give crude 2α-(6-hydroxycarbonyl-hex-cis-2-enyl)-3β-(3-hydroxy-prop-trans-1-enyl)-4α-(2-tetrahydropyranyloxy)-cyclopentan-1α-ol having the following physical characteristics:

IR (liquid film); $v$: 2930, 1720, 1240 and 1120 cm$^{-1}$;
NMR (CDCl$_3$ solution); δ: 5.70 – 5.25 (4H, $m$) and 4.62 (1H, $m$);
TLC (developing solvent methylene chloride:methanol = 19:1); Rf = 0.23.

The crude 6-carboxy compound thus obtained was dissolved in 40 ml. of methylene chloride, cooled to 0° C. and a solution of diazomethane in diethyl ether was added until the reaction mixture was coloured pale yellow. The reaction mixture was then concentrated under reduced pressure and the residue was subjected to column chromatography on silica gel using a mixture of ethyl acetate:cyclohexane (1:1) as eluent to give 2.87 g. of the title compound having the following physical characteristics:

IR (liquid film); $v$: 3420, 2930, 1740, 1435 and 1020 cm$^{-1}$;
NMR (CDCl$_3$ solution); δ: 5.75 – 5.20 (4H, $m$), 4.67 (1H, $m$), 4.20 – 3.30 (6H, $m$) and 3.67 (3H, $s$);
TLC (developing solvent ethyl acetate:cyclohexane = 2:1); Rf = 0.31.

REFERENCE EXAMPLE 24

2α-(6-Methoxycarbonyl-hex-cis-2-enyl)-3β-(2-formyl-eth-trans-1-enyl)-4α-(2-tetrahydropyranyloxy)-cyclopentan-1α-ol 3.8 g. of active manganese dioxide were added to a solution of 382 mg. of 2α-(6-methoxycarbonyl-hex-cis-2-enyl-3β-(3-hydroxy-prop-trans-1-enyl)-4α-(2-tetrahydropyranyloxy)-cyclopentan-1α-ol (prepared as described in Reference Example 23) in 30 ml. of methylene chloride, the mixture stirred at room temperature for 2 hours and filtered. The precipitate was washed thoroughly with acetone, and the filtrate and washing were combined and concentrated under reduced pressure. The residue was purified by column chromatography on silica gel using a mixture of ethyl acetate:benzene (1:4) as eluent to give 266 mg. of the title compound having the following physical characteristics:

IR (liquid film); $v$: 3450, 2930, 1737, 1688, 1632, 1435, 1125, 1022 and 977 cm$^{-1}$;
NMR (CDCl$_3$ solution); δ: 9.56 (1H, $d$), 6.82 and 6.79 (1H, $dd$, respectively), 6.20 and 6.18 (1H, each $dd$), 5.36 (2H, $m$), 4.58 (1H, $m$), 3.61 (3H, $s$) and 4.30 – 3.20 (4H, $m$);
TLC (developing solvent ethyl acetate:benzene = 1:2); Rf = 0.27.

REFERENCE EXAMPLE 25

1α-Acetoxy-2α-(6-methoxycarbonyl-hex-cis-2-enyl)-3β-(2-formyl-eth-trans-1-enyl)-4α(2-tetrahydropyranyloxy)-cyclopentane 380 mg. of 2α-(6-methoxycarbonyl-hex-cis-2-enyl)-3β-(2-formyl-eth-trans-1-enyl)-4α-(2-tetrahydropyranyloxy)-cyclopentan-1α-ol (prepared as described in Reference Example 24) were dissolved in 1.61 ml. of pyridine and 1.87 ml. of acetic anhydride were added and stirred at room temperature for 5 hours. The reaction mixture was concentrated under reduced pressure, the residue was dissolved in 50 ml. of ethyl acetate and 5 ml. of 0.05N hydrochloric acid were added. After separation into two layers, the organic layer was washed with an aqueous sodium chloride solution, dried over magnesium sulphate and concentrated under reduced pressure. The residue was purified by column chromatography on silica gel using a mixture of ethyl acetate:benzene (1:4) as eluent to give 380 mg. of the title compound having the following physical characteristics:

IR (liquid film); $v$: 2930, 1737, 1687, 1636, 1244, 1127 and 1030 cm$^{-1}$;
NMR (CDCl$_3$ solution ); δ: 9.56 (1H, $d$), 6.82 and 6.79 (1H, each $dd$), 6.26 and 6.23 (1H, each $dd$), 5.34 (2H, $m$), 5.11 (1H, $m$), 4.56 (1H, $m$), 4.27 – 3.25 (3H, $m$), 3.67 (3H, $s$), 2.09 (3H, $s$) and 3.00 – 1.26 (18H, $m$);
TLC (developing solvent ethyl acetate:benzene = 1:2); Rf = 0.50.

REFERENCE EXAMPLE 26

Methyl 9α-acetoxy-11α-(2-tetrahydropyranyloxy)-15(S)-hydroxy-15(S)-cyclohexyl-ω-pentanor-prosta-cis-5,trans-13-dienoate A solution of cyclohexylmagnesium bromide (prepared from 187 mg. of magnesium ribbon, 1.19 g. of bromocyclohexane and 8 ml. of diethyl ether) was added dropwise at 0° C. to a solution of 6.27 g. of 1α-acetoxy-2α-(6-methoxycarbonylhex-cis-2-enyl)-3β-(2-formyl-eth-trans-1-enyl)-4α-(2-tetrahydropyranyloxy)-cyclopentane (prepared as described in Reference Example 25) in 100 ml. of diethyl ether and the reaction mixture was stirred at that temperature for a further one hour. A saturated aqueous ammonium chloride solution was added and the solution extracted with ethyl acetate. The organic extracts were washed with water, dried over magnesium sulphate and concentrated under reduced pressure. The residue was purified by column chromatography on silica gel using a mixture of benzene and ethyl acetate (from 7:1 to 5:1) as eluent to give 1.28 g. of the title compound having the following physical characteristics:

IR (liquid film); ν: 3450, 2920, 2850, 1740, 1450, 1380, 1140, 1030 cm$^{-1}$;

NMR (CDCl$_3$ solution); δ: 5.8 – 4.9 (5H, m), 4.8 – 4.5 (1H, broad s), 4.3 – 3.2 (7H, m), 3.0 – 0.7 (30H, m);

TLC (developing solvent benzene:ethyl acetate = 2:1); Rf = 0.40.

EXAMPLE 23

9α,15(S)-Dihydroxy-11α-(2-tetrahydropyranyloxy)-15(S)-cyclohexyl-ω-pentanor-prosta-cis-5,trans-13-dienoic acid 12.0 ml. of a 2N aqueous potassium hydroxide solution was added to a solution of 750 mg. of methyl 9α-acetoxy-11α-(2-tetrahydropyranyloxy)-15(S)-hydroxy-15(S)-cyclohexyl-ω-pentanor-prosta-cis-5,trans-13-dienoate (prepared as described in Reference Example 26) in 12.0 ml. of methanol, and the reaction mixture was stirred at 40° C. for 1 hour and then diluted with chilled water, acidified with oxalic acid and extracted with ethyl acetate. The extracts were washed with an aqueous sodium chloride solution, dried over magnesium sulphate and concentrated under reduced pressure to give 605 mg. of the title compound having the following physical characteristics:

IR (liquid film); ν: 3400, 2950, 2850, 1720, 1030, 980 cm$^{-1}$;

NMR (CDCl$_3$ solution); δ: 5.9 – 5.2 (7H, m), 4.8 – 4.4 (1H, m), 4.3 – 3.3 (5H, m);

TLC (developing solvent methylene chloride:methanol = 20:1); Rf = 0.32.

EXAMPLE 24

9α,11α,15(S)-Trihydroxy-15(S)-cyclohexyl-ω-pentanor-prosta-cis-5,trans-13dienoic acid
[15(S)-Cyclohexyl-ω-pentanor-PGF$_2$]

160 mg. of 9α,15(S)-dihydroxy-11α-(2-tetrahydropyranyloxy)-15(S)-cyclohexyl-ω-pentanor-prosta-cis-5,trans-13-dienoic acid (prepared as described in Example 23) were dissolved in 6 ml. of a mixture of tetrahydrofuran, acetic acid and water (10:65:35) and the solution was stirred at 40° C. for 1 hour. The reaction mixture was diluted with 30 ml. of ethyl acetate, washed with an aqueous sodium chloride solution, dried over magnesium sulphate and concentrated under reduced pressure. The residue was purified by column chromatography on silica gel using a mixture of cyclohexane and ethyl acetate (1:1) as eluent to give 55 mg. of the title compound having the following physical characteristics:

IR (liquid film); ν: 3350, 3000, 2900, 2850, 2700–2300, 1710, 1450, 1410, 1380, 1240, 1200, 1100, 1050, 1005, 980, 900 cm$^{-1}$;

NMR (CDCl$_3$ + acetone-d$_6$ solution); δ: 5.65 – 5.0 (8H, m), 4.25 – 4.04 (1H, m), 4.04 – 3.65 (2H, m);

TLC (developing solvent chloroform:tetrahydrofuran:acetic acid = 10:2:1); Rf = 0.15;

Optical rotation: [α]$_D^{24}$ = +23.6° (c = 0.95, ethanol).

REFERENCE EXAMPLE 27

Methyl 9α-acetoxy-11α,15(S)-bis-(2-tetrahydropyranyloxy)-15(S)-cyclohexyl-ω-pentanor-prosta-cis-5,trans-13-dienoate 0.7 mg. of p-toluenesulphonic acid and 0.321 ml. of 2,3-dihydropyran were added to a solution of 360 mg. of methyl 9α-acetoxy-11α-(2-tetrahydropyranyloxy)-15(S)-hydroxy-15(S)-cyclohexyl-ω-pentanor-prosta-cis-5,trans-13-dienoate (prepared as described in Reference Example 26) in 6 ml. of methylene chloride and the reaction mixture was stirred at room temperature for 15 minutes. 2 drops of pyridine were added to the reaction mixture, which was washed with a saturated aqueous sodium bicarbonate solution and with an aqueous sodium chloride solution, dried over magnesium sulphate and concentrated under reduced pressure. The residue was purified by column chromatography on silica gel using a mixture of benzene and ethyl acetate (12:1) as eluent to give 235 mg. of the title compound having the following physical characteristics:

IR (liquid film); ν: 2950, 2860, 1740, 1260, 1030, 980 cm$^{-1}$;

NMR (CDCl$_3$ solution); δ: 5.8 – 5.2 (4H, m), 5.2 – 4.9 (1H, m), 4.9 – 4.5 (2H, m), 4.5 – 3.2 (9H, m);

TLC (developing solvent methylene chloride:methanol = 20:1); Rf = 0.87.

EXAMPLE 25

9α-Hydroxy-11α,15(S)-bis-(2-tetrahydropyranyloxy)-15(S)-cyclohexyl-ω-pentanor-prosta-cis-5,trans-13-dienoic acid 235 mg. of methyl 9α-acetoxy-11α,15(S)-bis-(2-tetrahydropyranyloxy)-15(S)-cyclohexyl-ω-pentanor-prosta-cis-5,trans-13-dienoate (prepared as described in Reference Example 27) were dissolved in a mixture of 0.7 ml. of a 4N aqueous potassium hydroxide solution and 3 ml. of methanol and the solution stirred at room temperature for one hour. The reaction mixture was acidified with an aqueous oxalic acid solution and extracted with ethyl acetate. The extracts were washed with water and an aqueous sodium chloride solution, dried over magnesium sulphate and concentrated under reduced pressure to give 215 mg. of the title compound having the following physical characteristics:

IR (liquid film); ν: 3450, 3000, 2925, 2850, 2700–2300, 1710, 1445, 1350, 1265, 1205, 1190, 1140, 1125, 1080, 1030, 1010, 980, 915, 765 cm$^{-1}$;

NMR (CDCl$_3$ solution); δ: 6.6 – 5.85 (2H, m), 5.7 – 4.9 (4H, m), 4.9 – 4.4 (2H, m), 4.35 – 3.15 (7H, m);

TLC (developing solvent benzene:ethyl acetate = 2.3); Rf = 0.20.

REFERENCE EXAMPLE 28

Methyl 9α-acetoxy-11α-(2-tetrahydropyranyloxy)-15(S)-hydroxy-15(S)-cyclopentyl-ω-pentanor-prosta-cis-5,trans-13dienoate A solution of cyclopentylmagnesium bromide (prepared from 207 mg. of magnesium ribbon, 1.29 g. of bromocyclopentane and 10 ml. of diethyl ether) was added dropwise at 0° C. to a solution of 7.07 g. of 1α-acetoxy-2α-(6-methoxycarbonylhex-cis-2-enyl)-3β-(2-formyl-eth-trans-1-enyl)-4α-(2-tetrahydropyranyloxy)-cyclopentane (prepared as described in Reference Example 25) in 100 ml. of diethyl ether and the reaction mixture was stirred at that temperature for a further one hour. A saturated aqueous ammonium chloride solution was added and the solution extracted with ethyl acetate. The organic extracts were washed with water, dried over magnesium sulphate and concentrated under reduced pressure. The residue was purified by column chromatography on silica gel using a mixture of benzene and ethyl acetate (from 7:1 to 5:1) as eluent to give 1.3 g. of the title compound having the following physical characteristics:

IR (liquid film); $\nu$: 2950, 2860, 1740 cm$^{-1}$;

NMR (CDCl$_3$ solution); $\delta$: 5.8 – 4.8 (5H, $m$), 4.8 – 4.4 (1H, $m$), 4.3 – 3.2 (7H, $m$);

TLC (developing solvent benzene:ethyl acetate = 2:1); Rf = 0.30.

EXAMPLE 26

9α,15(S)-Dihydroxy-11α-(2-tetrahydropyranyloxy)-15(S)-cyclopentyl-ω-pentanor-prosta-cis-5,trans-13dienoic acid 1.13 ml. of a 2N aqueous potassium hydroxide solution were added to a solution of 300 mg. of methyl 9α-acetoxy-11α-(2-tetrahydropyranyloxy)-15(S)-hydroxy-15(S)-cyclopentyl-ω-pentanor-prosta-cis-5,trans-13-dienoate (prepared as described in Reference Example 28) in 6.0 ml. of methanol, and the reaction mixture was stirred at 40° C. for 1 hour and then diluted with chilled water, acidified with oxalic acid and extracted with ethyl acetate. The extracts were washed with an aqueous sodium chloride solution, dried over magnesium sulphate and concentrated under reduced pressure to give 306 mg. of the titlecompound having the following physical characteristics:

IR (liquid film); $\nu$: 3400, 2950, 2850, 1720, 1030, 980 cm$^{-1}$;

NMR (CDCl$_3$ solution); $\delta$: 5.9 – 5.2 (7H, $m$), 4.9 – 4.4 (1H, $m$), 4.3 – 3.2 (5H, $m$);

TLC (developing solvent methylene chloride:methanol = 20:1); Rf = 0.33.

EXAMPLE 27

9α,11α,15(S)-Trihydroxy-15(S)-cyclopentyl-ω-pentanor-prosta-cis-5,trans-13dienoic acid
[15(S)-Cyclopentyl-ω-pentanor-PGF$_2$ ]

300 mg. of 9α,15(S)-dihydroxy-11α-(2-tetrahydropyranyloxy)-15(S)-cyclopentyl-ω-pentanor-prosta-cis-5,trans-13-dienoic acid (prepared as described in Example 26) were dissolved in a mixture of 4 ml. of tetrahydrofuran, 0.29 ml. of 12N hydrochloric acid and 2.15 ml. of water and the solution was stirred at 40° C. for 1 hour. The reaction mixture was then diluted with 50 ml. of ethyl acetate, washed with an aqueous sodium chloride solution, dried over magnesium sulphate and concentrated under reduced pressure. The residue was purified by column chromatography on silica gel using a mixture of cyclohexane and ethyl acetate (from 3:1 to 3:2) as eluent to give 85 mg. of the title compund having the following physical characteristics:

IR (KBr tablet); $\nu$: 3260, 2900, 2850, 1700, 1410, 1340, 1190 cm$^{-1}$;

NMR (CDCl$_3$ + CD$_3$OD solution); $\delta$: 5.7 – 5.1 (4H, $m$), 4.72 – 4.15 (4H, broad $s$), 4.25 – 4.00 (1H, $m$), 4.00 – 3.60 (2H, $m$);

TLC (developing solvent chloroform:tetrahydrofuran: acetic acid = 10:2:1); Rf = 0.16.

REFERENCE EXAMPLE 29

Methyl 9α-acetoxy-11α,15(S)-bis-(2-tetrahydroyranyloxy)-15(S)-cyclophenyl-ω-pentanor-prosta-cis-5,trans-13-dienoate 1.60 mg. of p-toluenesulphonic acid and 0.467 ml. of 2,3-dihydropyran were added to a solution of 994 mg. of methyl 9α-acetoxy-11α-(2-tetrahydroyranyloxy)-15(S)-hydroxy-15(S)-cyclypentyl-ω-pentanor-prosta-cis-5,trans-13dienoate (prepared as described in Reference Example 28) in 10 m. of methylene chloride and the reaction mixture was stirred at room temperature for 15 minutes. 2 drops of pyridine were added to the reaction mixture, which was washed successively with a saturated sodium bicarbonate solution and an aqueous sodium chloride solution, dried over magnesium sulphate and concentrated under reduced pressure to give 1.16 g. of the title compound having the following physical characteristics:

IR (liquid film); $\nu$: 2950, 2860, 1740, 1260, 1030, 980 cm$^{-1}$;

NMR (CDCl$_3$ solution); $\delta$: 5.8 – 4.22 (4H, $m$), 5.22 – 4.9 (1H, $m$), 4.9 – 4.5 (2H, $m$), 4.5 – 3.2 (9H, $m$);

TLC (developing solvent methylene chloride:methanol = 20:1); Rf = 0.88.

EXAMPLE 28

9α-Hydroxy-11α,15(S)-bis-(2-tetrahydropyranyloxy)-15(S)-cycleopentyl-ω-pentanor-prosta-cis-5,trans-13dienoic acid 1.16 g. of methyl 9α-acetoxy-11α,15(S)-bis-(2-tetrahydropyranyloxy)-15(S)-cyclopentyl-ω-pentanor-prosta-cis-5,trans-13dienoate (prepared as described in Reference Example 29) were dissolved in a mixture of 0.68 g. of potassium hydroxide, 3.77 ml. of water, 7.2 ml. of ethanol and 1.9 ml. of tetrahydrofuran and the solution stirred at room temperature for 1 hour. The reaction mixture was acidified with an aqueous oxalic acid solution and extracted with ethyl acetate. The extracts were washed with water and an aqueous sodium chloride solution, dried over magnesium sulphate and concentrated under reduced pressure. The residue was purified by column chromtoraphy on silica gel using a mixture of ethyl acetate and diethyl ether (1:1) as eluent to give 0.91 g. of the title compound having the following physical characteristics:

IR (liquid film); $\nu$: 340, 3000, 2930, 2850, 2700–2300, 1710, 1445, 1350, 1205, 1190, 1140, 1125, 1080, 1030, 980 cm$^{-1}$;

NMR (CDCl$_3$ solution); $\delta$: 6.62 – 5.85 (2H, $m$), 5.70 – 4.91 (4H, $m$), 4.91 – 4.28 (2H, $m$), 4.32 – 3.15 (7H, $m$);

TLC (developing solvent methylene chloride:methanol = 20:1); Rf = 0.24.

REFERENCE EXAMPLE 30

Methyl 9α-acetoxy-11α-(2-tetrahydropyranyloxy)-15($\xi$)-hydroxy-15-cyclohexyl-ω-pentanor-prosta-cis-5,trans-13-dienoate A solution of cyclohexylmagnesium bromide (prepared from 187 mg. of magnesium ribbon, 1.19 g. of bromocyclohexane and 8 ml. of diethyl ether) was added dropwise at 0° C. to a solution of 6.27 g. of 1α-acetoxy-2α-(6-methoxycarbonylhex-cis-2-enyl)-3β-(2-formyl-eth-trans-1-enyl)-4α-(2-tetrahydropyranlyoxy)-cyclopentane (prepared as described in Reference Example 25) in 100 ml. of diethyl ether and the reaction mixture was stirred at that temperature for a further one hour. A saturated aqueous ammonium chloride solution was added and the solution extracted with ethyl acetate. The organic extracts were washed with water, dried over magnesium sulphate and concentrated under reduced pressure to give 8.0 g. of the title compound having the following physical characteristics:

IR (liquid film); ν: 3450, 2920, 2850, 1740, 1450, 1380, 1140, 1030 cm⁻¹;

NMR (CDCl₃ solution); δ: 5.8 – 4.9 (5H, m), 4.8 – 4.5 (1H, broad s), 4.3 – 3.2 (7H, m), 3.0 – 0.7 (30H, m);

TLC (developing solvsent benzene:ethyl acetate = 2:1); Rf = 0.4 and 0.5.

REFERENCE EXAMPLE 31

Methyl 9α-acetoxy-11α-(2-tetrahydropanyloxy)-15-oxo-15-cyclohexyl-ω-pentanor-prosta-cis-5,trans-13dienoate A solution of 8.0 g. of methyl b 9α-acetoxy-11α-(2-tetrahydropyranyloxy)-15(ξ)-hydroxyl-15-cyclohexyl-ω-pentanor-prosta-cis-5,trans-13-dienoate (prepared as described in Reference Example 30) in 175 ml. of methylene chloride was cooled to 0° C. 175 ml. of a chromic acid solution (prepared by dissolving 8 g. of chromium trioxide, 38.6 g. of manganese sulphate and 8.92 ml. of sulphuric acid in water to a total volume of 200 ml.) were added to the solution, which was stirred vigorously at 0° C. for 1 hour. The reaction mixture was extracted with diethyl ether and the extracts were washed with water, dried over magnesium sulphate and concentrated under reduced pressure. The residue was purified by column chromatography on silica gel using a mixture of benzene and ethyl acetate (12:1) as eluant to give 3.91 g. of the title compound having the following physical characteristics:

IR (liquid film); ν: 2920, 2850, 1740, 1695, 1665, 1630, 1450, 1380, 1250, 1140 cm⁻¹;

NMR (CDCl₃ solution); δ- 6.85 (1H, dd), 6.32 (1H, d), 5.7 – 4.5 (1H, broad s), 4.3 – 3.2 (6H, m);

TLC (developing solvent benzene:ethyl acetate = 4:1); Rf = 0.15.

REFERENCE EXAMPLES 32

Methyl 9α-acetoxy-11α-(2-tetrahydropyranyloxy)-15(ξ)-hydroxy-15-cyclohexyl-ω-tetranor-prosta-cis-5,trans-13-dienoate 9.2 ml. of a 1 1Nsolution of methylmagnesium bromide in diethyl ether were added dropwise at 0° C. to a solution of 3.91 g. of methyl 9α-acetoxy-1α-(2-tetrahydropyranyloxy)-15-oxo-15-cyclohexyl-ω-pentanor-prosta-cis-5,trans-13-dienoate (prepared as described in Reference Example 31) in 100 ml. of diethyl ether, and the reaction mixture was stirred for 1 hour. A saturated aqueous ammonium chloride solution was then added to the reaction mixture, which was extracted with ethyl acetate. The organic extracts were washed with an aqueous sodium chloride solution, dried over magnesium sulphate and concentrated under reduced pressure. The residue was purified by column chromatography on silica bel using a mixture of benzene and ethyl acetate (6:1) as eluent to give 2.05 g. of the title compound having the following physical characteristics:

IR (liquid film); ν: 3470, 2920, 2840, 1740, 1450, 1380, 1250, 1140, 1030, 980 cm⁻¹;

NMR (CDCl₃ solution); δ: 5.8 – 5.0 (5H, m), 4.85 – 4.5 (1H, m), 4.3 – 3.3 (6H, m), 1.26 (3H, s).

EXAMPLE 29

9α,15(ξ)-Dihydroxy-11α-(2-tetrahydropyranyloxy)-15-cyclohexyl-ω-tetranor-prosta-cis-5,trans-13-dienoic acid 6.0 ml. of a 2N aqueous potassium hydroxide solutin were added to a solution of 379 mg. of methyl 9α-acetoxy-11α-(2-tetrahydropyranyloxy)-15(ξ)-hydroxy-15-cyclohexyl-ω-tetranor-prosta-cis-5,trans-13-dienoate (prepared as described in Reference Example 32) in 6.0 ml. of methanol, and the reaction mixture was stirred at 40° C. for 1 hour and then diluted with chilled water, acidified with oxalic acid and extractedwith ethyl acetate. The extracts were washed with an aqueous sodium chloride solution, dried over magnesium sulphate and concentrated under reduced pressure to give 317 mg. of the title compound having the following physical characteristics:

TLC (developing solvent benzene:ethyl acetate = 2:1); Rf = 0.14.

EXAMPLE 30

9α,11α,15(ξ)-Trihydroxy-15-cyclohexyl-ω-tretranor-prosta-cis-5,trans-13-dienoic acid [15(ξ)-Cyclohexyl-ω-tetranor-PGF₂ ]

317 mg. of 9α,15(ξ)-dihydroxy-11α-(2-tetrahydropyranyloxy)-15-cyclohexyl-ω-tetranor-prosta-cis-5,trans-13-dienoic acid (prepared as described in Example 29) were dissolved in 11 ml. of a mixture of tetrahydrofuran, acetic acid and water (10:65:35) and the solution was stirred at 40° C. for one hour. The reaction mixture was then diluted with 50 ml. of ethyl acetate, washed with an aqueous sodium chloride solution, dried over magnesium sulphate and concentrated under reduced pressure. The residue was purified by column chromatography on silica gel using a mixture of cyclohexane and ethyl acetate (1:1) as eluent to give 110 mg. of the title compound having the folowing physical characteristics:

IR (liquid film); ξ: 3400, 2920, 2850, 2650–2200, 1710, 1450, 1380, 1250, 1050, 980 cm⁻¹;

NMR (CDCl₃ solution); δ: 5.8 – 4.2 (4H, m), 4.85 – 3.90 (4H, broad s), 4.15 (1H, m), 3.92 (1H, m), 2.5 – 1.95 (8H, m), 1.95 – 1.5 (9H, m), 1.22 (3H, s);

TLC (developing solvent chloroform:tetrahydrofuran: acetic acid = 10:2:1); Rf = 0.28.

EXAMPLE 31

9-Oxo-11α-(2-tetrahydropyranyloxy)-15(ξ)-hydroxy-15-cyclohexyl-ω-tetranor-prosta-cis-5,trans-13-dienoic acid 1.39 ml. of pyridine and 864 mg. of chromium trioxide were added to 20 ml. of methylene chloride and the reaction mixture was stirred at room temperature under an atmosphere of nitrogen for 15 minutes. 1.8 g. of infusorial earth were then added. The reaction mixture was cooled to 0° C. and then at that temperature a solution of 499 mg.of 9α,15(ξ)-dihydroxy-11α-(2-tetrahydropyranyloxy)-15-cyclohexyl-ω-tetranor-prosta-cis-5,trans-13-dienoic acid (prepared as described in Example 29) in 10 ml. of methylene chloride was added. After stirring for 5 minutes, 4.8 g. of sodium bisulphate were added and stirring continued for a further 10 minutes. The reaction mixture was filtered through a pad of magnesium sulphate and the filtrate was concentrated under reduced pressure. The residue was purified by column chromatography on silica gel using a mixture of benzene and ethyl acetate (2:1) as eluent to give 257 mg. of the title compound having the following physical characteristics:

NMR (CDCl$_3$ solution); δ: 5.8 – 5.2 (4H, m), 4.9 – 4.5 (2H, m), 3.9 – 3.3 (5H, m);

TLC (developing solvent chloroform:tetrahydrofuran: acetic acid = 10:2:1); Rf = 0.49.

EXAMPLE 32

9-Ox0-11α,15(ξ)-dihydroxy-15-cyclohexyl-ω-tetranor-prostacis-5,-trans-13-dienoic acid
[15(ξ)-Cyclohexyl-ω-tetranor-PGE$_2$]

203 mg. of 9-oxo-11α-(2-tetrahydropyranyloxy)-15(ξ)-hydroxy-15-cyclohexyl-ω-tetranor-prosta-cis-5,trans-13-dienoic acid (prepared as described in Example 31) were dissolved in 7.2 ml. of a mixture of tetrahydrofuran, acetic acid and water (10:65:35) and the solution was stirred at 40° C. for one hour. The reaction mixture was diluted with 40 ml. of ethyl acetate, washed with an aqueous sodium chloride solution, dried over magnesium sulphate and concentrated under reduced pressure. The residue was purified by column chromatography on silica gel using a mixture of cyclohexane and ethyl acetate (2:1) as eluent to give 79 mg. of the title compound having the following physical characteristics:

IR (liquid film); : 3400, 2920, 2840, 2650 – 2200, 1740, 1710, 1450, 1250, 1160, 1080, 980, 890, 760 cm$^{-1}$; NMR (CDCl$_3$ solution); δ: 5.7 – 5.5 (2H, m), 5.5 – 5.25 (2H, m), 5.2 – 4.70 (3H, broad s), 4.25 – 4.0 (1H, m), 2.95 – 2.55 (1H, dd), 1.25 (3H, s);

TLC (developing solvent chloroform:tetrahydrofuran: acetic acid = 10:2:1); Rf = 0.32.

REFERENCE EXAMPLE 33

METHYL 9α-acetoxy-11α, 15(ξ)-bis-(2-tetrahydropyranyloxy)-15-cyclohexyl-ω-tetranor-prosta-cis-5,-trans-13-dienoate 1.29 mg. of p-toluenesulphonic acid and 0.616 ml. of 2,3-dihydropyran were added to a solution of 706 mg. of methyl 9α-acetoxy-11α-(2-tetrahydropyranyloxy-15(ξ)-hydroxy-15-cyclohexyl-ω-tetranor-prosta-cis-5,-trans-13-dienoate (prepared as described in Reference Example 32) in 10 ml. of methylene chloride and the reaction mixture was stirred at room temperature for 15 minutes. 2 drops of pyridine were added to the reaction mixture, which was washed successively with a saturated aqueous sodium bicarbonate solution and with an aqueous sodium chloride solution, dried over magnesium sulphate and concentrated under reduced pressure. The residue was purified by column chromatography on silica gel using a mixture of benzene and ethyl acetate (12:1) as eluent to give 450 mg. of the title compound having the following physical characteristics:

NMR (CDCl$_3$ solution); δ: 5.56 – 4.95 (4H, m), 4.80 – 4.45 (2H, m), 4.12 – 3.20 (6H, m), 3.66 (3H, s); TLC (developing solvent benzene:ethyl acetate = 4:1); Rf = 0.67.

REFERENCE EXAMPLE 34

Methyl 9α-acetoxy-11α,15(ξ)-bis-(2-tetrahydropyranyloxy)-15-cyclohexyl-ω-tetranor-prost-trans-13-enoate 94 mg. of 5% (w/w) palladium on carbon were suspended in 30 ml. of methanol, the air in the apparatus was replaced by hydrogen, and a solution of 450 mg. of methyl 9α-acetoxy-11α,15(ξ)-bis-(2-tetrahydropyranyloxy)-15-cyclohexyl-ω-tetranor-prosta-cis-5,trans-13-dienoate (prepared as described in Reference Example 33) in 10 ml. of methanol was added thereto. Catalytic reduction of the compound was carried out at room temperature under ambient pressure for 10 minutes. After completion of the reaction, the catalyst was filtered off and the filtrate was concentrated under reduced pressure to give 450 mg. of the title compound having the following physical characteristic:

NMR (CDCl$_3$ solution); δ: 5.70 – 5.25 (2H, m), 5.25 – 5.00 (1H, m), 4.8 – 4.5 (2H, m), 4.3 – 3.2 (8H, m).

EXAMPLE 33

9α-Hydroxy-11α,15(ξ)-bis-(2-tetrahydropyranyloxy-15-cyclohexyl-ω-tetranor-prost-trans-13-enoic acid 450 mg. of methyl 9α-acetoxy-11α,15(ξ)-bis-(2-tetrahydropyranyloxy-15-cyclohexyl-ω-tetranor-prost-trans-13-enoate (prepared as described in Reference Example 34) were dissolved in a mixture of 1.3 ml. of a 4N aqueous potassium hydroxide solution and 4 ml. of methanol and the solution stirred at room temperature for 1 hour. The reaction mixture was acidified with an aqueous oxalic acid solution and extracted with ethyl acetate. The extracts were washed with water and an aqueous sodium chloride solution, dried over magnesium sulphate and concentrated under reduced pressure to give 415 mg. of the title compound having the following physical characteristic:

TLC (developing solvent benzene:ethyl acetate = 2:1); Rf = 0.15.

EXAMPLE 34

9-Oxo-11α, 15(ξ)-bis-(2-tetrahydropyranyloxy)-15-cyclohextyl-ω-tetranor-prost-trans-13-enoic acid 1.11 ml. of pyridine and 692 mg. of chromium trioxide were added to 16 ml. of methylene chloride and the reaction mixture was stirred at room temperature under an atmosphere of nitrogen for 15 minutes. 1.4 g. of infursorial earth were added thereto. The reaction mixture was cooled to 0° C. and then at that temperature a solution of 410 mg. of 9α -hydroxy-11α,15(ξ)-bis-(2-tetrahydropyranyloxy)-15-cyclohexyl-ω-tetranor-prosttrans-13-enoic acid (prepared as described in Example 33) in 8 ml. of methylene chloride was added. After stirring for 5 minutes, 3.9 g. of sodium bisulphate were added and stirring continued for a further 10 minutes. The reaction mixture was filtered through a pad of magnesium sulphate and the filtrate was concentrated under reduced pressure. The residue was purified by column chromatography on silica gel using a mixture of benzene and ethyl acetate (2:1) as eluent to give 284 mg. of the title compound having the following physical characteristics: NMR (CDCL$_3$ solution); δ: 5.75 – 5.30 (2H, m), 4.8 – 4.5 (2H, m), 4.2 – 3.2 (6H, m); TLC (developing solvent benzene:ethyl acetate = 1:1); Rf = 0.48.

EXAMPLE 35

9-Oxo-11α, 15(ξ)-dihydroxy-15-cyclohexyl-ω-tetranor-prosttrans-13-enoic acid [15(ξ)-Cyclohexyl-ω-tetranor-PGE₁]

284 mg. of 9-oxo-11α, 15(ξ)-bis-(2-tetrahydropyranyloxy)-15-cyclohexyl-ω-tetranor-prost-trans-13-enoic aicd (prepared as described in Example 34) were dissolved in 10 ml. of a mixture of tetrahydrofuran, acetic acid and water (10:65:35) and the reaction mixture was stirred at 40° to 45° C. for 2 hours, diluted with 60 ml. of ethyl acetate, washed with an aqueous sodium chloride solution, dried over magnesium sulphate and concentrated under reduced pressure. The residue was purified by column chromatography on silica gel using a mixture of cyclohexane and ethyl acetate (2:1) as eluent to give 110 mg. of the title compound having the following physical characteristics: IR (liquid film); $v$:3400, 2920, 2850, 2750 – 2400, 1740, 1720, 1450, 1250, 980 cm⁻; NMR (CDCL₃ solution), $\delta$: 5.85 – 5.50 (2H, $m$), 4.75 – 4.50 (3H, broad $s$), 4.20 – 3.95 (1H, $m$), 2.90 – 2.55 (1H, $dd$), 1.28 (3H, $s$);

TLC (developing solvent chloroform:tetrahydrofuran: acetic acid = 10:2:1); Rf = 0.34.

EXAMPLE 36

Methyl 9α-hydroxy-11α,15(S)-bis-(2-tetrahydropyranyloxy)-15(S)-cyclohexyl-ω-pentanor-prost-trans-13-enoate To a solution of 3.4 g. of 9α-hydroxy-11α, 15(S)-bis-(2-tetrahydropyranyloxy)-15(S)-cyclohexyl-ω-pentanor-prost-trans-13-enoic acid (prepared as described in Example 6) in 20 ml. of diethyl ether, there was added dropwise a solution of freshly prepared diazomethane in diethyl ether at 0° C. until a light-yellow colour in the reaction mixture persisted. The reaction mixture was then concentrated under reduced pressure to give 2.4 g. of the title compound having the following physical characteristics:-

NMR (CDCl₃ solution); $\delta$: 5.70 – 5.20 (2H, $m$), 4.85 – 4.50 (2H, $m$), 4.25 – 3.10 (10H, $m$);

TLC (developing solvent methylene chloride:methanol = 20:1); Rf = 0.43

EXAMPLE 37

Methyl 9α-hydroxy-11α, 15(S)-bis-(2-tetrahydropyranyloxy)-15(S)-cyclohexyl-ω-pentanor-prosta-trans-2,trans-13-dienoate 1.403 ml. of diisopropylamine were dissolved in 30 ml. of dry tetrahydrofuran and cooled to −70° C. 6.23 ml. of a 1.6M solution of n-butyllithium in n-hexane were added dropwise to the solution and the reaction mixture was stirred for 15 minutes at −70° C. To the solution thus obtained, a solution of 2.4 g. of methyl 9α-hydroxy-11α, 15(S)-bis-(2-tetrahydropyranyloxy)-15(S)-cyclohexyl-ω-pentanor-prost-trans-13-enoate (prepared as described in Example 36) in 15 ml. of dry tetrahydrofuran was added dropwise at −70° C. and stirred for 20 minutes at the same temperature. A solution of 3.264 g. of diphenyldiselenide in 20 ml. of dry tetrahydrofuran was added to the reaction mixture dropwise at −70° C. and then stirred for one hour at the same temperature. The temperature of the reaction mixture was then raised to room temperature. The reaction mixture was poured into a small amount of saturated aqueous ammonium chloride solution and extracted with ethyl acetate. The organic layer was washed with water and an aqueous sodium chloride solution, dried over magnesium sulphate and concentrated under reduced pressure. The residue was purified by column chromatography on silica gel using a mixture of benzene and ethyl acetate (10:1) as eluent to give 2.145 g. of methyl 9α-hydroxy-11α,15(S)-bis-(2-tetrahydropyranyloxy)-15(S)-cyclohexyl-2-phenylselenenyl-ω-pentanor-prost-trans-13-enoate having the following physical characteristics:- NMR (CDCl₃ solution); $\delta$: 7.80 – 7.10 (5H, $m$), 5.65 – 5.10 (2H, $m$), 4.60 – 4.40 (2H, $m$), 4.30 – 3.10 (11H, $m$);

TLC (developing solvent benzene:ethyl acetate = 2:1); Rf = 0.44

The phenylselenenyl compound, thus obtained, was dissolved in 47 ml. of a mixture of ethyl acetate and tetrahydrofuran (1:3) and 1.55 ml. of hydrogen peroxide were added to the solution, which was then stirred at 30° to 32° C. for 30 minutes and diluted with 100 ml. of ethyl acetate. The mixture was washed with water and an aqueous sodium chloride solution, dried over magnesium sulphate and concentrated under reduced pressure to give 1.685 g. of the title compound having the following physical characteristics:-

IR (liquid film); $v$: 3450, 2930, 2850, 1730, 1660, 980 cm¹¹⁶;

NMR (CDCl₃ solution); $\delta$: 7.30 – 6.50 (1H, $t$-$d$), 6.10 – 5.20 (3H, m) 4.90 – 4.50 (2H, m), 4.40 – 3.10 (10H, m);

TLC (developing solvent benzene:ethyl acetate = 2:1); Rf = 0.32.

EXAMPLE 38

9α-Hydroxy-11α,15(S)-bis-(2-tetrahydropyranyloxy)-15(S)-cyclohexyl-ω-pentanor-prosta-trans-2,trans-13-dienoic acid A solution of 492 mg. of potassium hydroxide in 5.4 ml. of water was added to a solution of 1.685 g. of methyl 9α-hydroxy-11α,15(S)-bis-(2-tetrahydropyranyloxy)-15(S)-cyclohexyl-ω-pentanor-prosta-trans-2,trans-13-dienoate (prepared as described in Example 37) in a mixture of 11 ml. of ethanol and 2.7 ml. of tetrahydrofuran and stirred at 40° C. for 2 hours. The reaction mixture was concentrated under reduced pressure and extracted with ethyl acetate. The extracts were washed with water and an aqueous sodium chloride solution, dried over magnesium sulphate and concentrated under reduced pressure to give 1.52 g. of the title compound having the following physical characteristic:-

TLC (developing solvent methylene chloride:methanol = 20:1); Rf = 0.19.

EXAMPLE 39

9-Oxo-11α,15(S)-bis-(2-tetrahydropyranyloxy)-15(S)-cyclohexyl-ω-pentanor-prosta-trans-2,trans-13-dienoic acid 1.52 g. of 9α-hydroxyl-11α,15(S)-bis-(2-tetrahydropyranyloxy)-15(S)-cyclohexyl-ω-pentanor-prosta-trans-2,trans-13-dienoic acid (prepared as described in Example 38) were dissolved in 20 ml. of diethyl ether and cooled to 0° to −5° C. Then a chromic acid solution (prepared from 3.345 g. of maganese sulphate, 715 mg. of chromium trioxide, 0.794 ml. of sulphuric acid and 17.6 ml. of water) was added to the solution and the reaction mixture was stirred vigorously at 0° C. for 2 hours and then separated into two layers. The aqueous layer was extracted with diethyl ether. The combined organic layer was washed with water and an aqueous sodium chloride solution, dried over magnesium sulphate and concentrated under reduced pressure to give 1.25 g. of the title compound having the following physical characteristic:-

TLC (developing solvent methylene chloride:methanol = 20:1); Rf = 0.31.

EXAMPLE 40

9Oxo-11α,15(S)-dihydroxy-15(S)-cyclohexyl-ω-pentanor-prosta-trans-2,trans-13-dienoic acid [15(S)-Cyclohexyl-ω-pentanor-trans-$\Delta^2$-prostaglandin $E_1$]

1.25 g. of 9-oxo-11α,15(S)-bis-(2-tetrahydropyranyloxy)-15(S)-cyclohexyl-ω-pentanor-prosta-trans-2,trans-13-dienoic acid (prepared as described in Example 39) were dissolved in a mixture of 11.3 ml. of acetic acid, 6.1 ml. of water and 4 ml. of tetrahydrofuran and stirred at 45° C. for 3 hours. The reaction mixture was then poured into ice-water and extracted with ethyl acetate. The extracts were washed with water and an aqueous sodium chloride solution, dried over magnesium sulphate and concentrated under reduced pressure. The residue was subjected to column chromatography on silica gel using a mixture of cyclohexane and ethyl acetate (1:1) as eluent to give 652 mg. of the title compound having the following physical characteristics:-

IR (liquid film); ν: 3350, 2900, 2850, 1740, 1690, 1650, 1440, 970 cm[116]; NMR (CDCl$_3$ solution); δ: 7.20 – 6.70 (1H, d-t), 5.90 – 5.00 (6H, m), 4.30 – 3.60 (2H, m);

TLC (developing solvent chloroform:tetrahydrofuran: acetic acid = 10:2:1); Rf = 0.32.

EXAMPLE 41

Methyl 9α-hydroxy-11α,15(S)-bis-(2-tetrahydropyranyloxy)-15(S)-cyclopentyl-ω-pentanor-prost-trans-13-enoate To a solution of 1.4 g. of 9α-hydroxy-11α,15(S)-bis-(2-tetrahydropyranyloxy)-15(S)-cyclopentyl-ω-pentanor- prost-trans-13-enoic acid (prepared as described in Example 21)in 10 ml. of diethyl ether, there was added dropwise a freshly prepared solution of diazomethane in diethyl ether at 0° C. until a light-yellow colour in the reaction mixture persisted. The reaction mixture was then concentrated under reduced pressure to give 1.04 g. of the title compound having the following physical characteristics:

NMR (CDCl$_3$ solution); δ: 5.70 – 5.20 (2H, m), 4.85 – 4.52 (2H, m), 4.24 – 3.20 (10H, m);

TLC (developing solvent methylene chloride:methanol = 20:1); Rf = 0.45.

EXAMPLE 42

Methyl 9α-hydroxy-11α,15(S)-bis-(2-tetrahydropyranyloxy)-15(S)-cyclopentyl-ω-pentanor-prosta-trans-2,trans-13-dienoate 0.65 ml. of diisobutylamine was dissolved in 13 ml. of dry tetrahydrofuran and cooled to −70° C. 3.7 ml. of a 1.25N solution of n-butyllithium in n-hexane were added dropwise to the solution and the reaction mixture was stirred for 20 minutes at −70° C. To the solution thus obtained, a solution of 1.04 g. of methyl 9α-hydroxy-11α,15(S)-bis-(2-tetrahydropyranyloxy)-15(S)-cyclopentyl-ω-pentanor-prost-trans-13-enoate (prepared as described in Example 41) in 7 ml. of dry tetrahydrofuran was added dropwise at −70° C. and stirred for 20 minutes at the same temperature. A solution of 1.52 g. of diphenyldiselenide in 8 ml. of dry tetrahydrofuran was added to the reaction mixture dropwise at −70° C. and then stirred for one hour at the same temperature. The temperature was then raised to room temperature. The reaction mixture was poured into a small amount of saturated aqueous ammonium chloride solution and extracted with ethyl acetate. The extracts were washed with water and an aqueous sodium chloride solution, dried over magnesium sulphate and concentrated under reduced pressure. The residue was purified by column chromatography on silica gel using a mixture of benzene and ethyl acetate (7:1) as eluent to give 989 mg. of methyl 9α-hydroxy-11α,15(S)-bis-(2-tetrahydropyranyloxy)-15(S)-cyclopentyl-2-phenylselenenyl-ω-pentanor-prost-trans-13-enoate having the following physical characteristics:-

TLC (developing solvent benzene:ethyl acetate = 2:1); Rf = 0.47.

The phenylselenenyl compound thus obtained was dissolved in 30 ml. of a mixture of ethyl acetate and tetrahydrofuran (1:3) and 1.1 ml. of hydrogen peroxide were added to the solution, which was then stirred at 30° to 32° C. for 30 minutes and diluted with 100 ml. of ethyl acetate. The mixture was washed with water and an aqueous sodium chloride solution, dried over magnesium sulphate and concentrated under reduced pressure to give 707 mg. of the title compound having the following physical characteristics:-

NMR (CCl$_4$ solution); δ: 7.10 – 6.50 (1H, td), 6.0 – 5.10 (3H, m), 4.80 – 4.30 (2H, m), – 3.00 (10H, m);

TLC (developing solvent benzene:ethyl acetate = 2:1); Rf = 0.34.

EXAMPLE 43

9α-Hydroxy-11α,15(S)-bis-(2-tetrahydropyranyloxy)-15(S)-cyclopentyl-ω-pentanor-prosta-trans-2,trans-13-dienoic acid A solution of 222 mg. of potassium hydroxide in 2.4 ml. of water was added to a solution of 707 mg. of methyl 9α-hydroxy-11α,15(S)-bis-(2-tetrahydropyranyloxy)-15(S)-cyclopentyl-ω-pentanor-prosta-trans-2,trans-13-dieonate (prepared as described in Example 42)in a mixture of 5 ml. of ethanol and 1.2 ml. of tetrahydrofuran and stirred at 40° to 50° C. for 1 hour. The reaction mixture was concentrated under reduced pressure and extracted with ethyl acetate. The extracts were washed with water and an aqueous sodium chloride solution, dried over magnesium sulphate and concentrated under reduced pressure to give 622 mg. of the title compound having the following physical characteristic:-

TLC (developing solvent methylene chloride:methanol = 20:1); Rf = 0.16.

EXAMPLE 44

9-Oxo-11α,15(S)-bis-(2-tetrahydropyranyloxy)-15(S)-cyclopentyl-ω-pentanor-prosta-trans-2,trans-13-dienoic acid 622 mg. of 9α-hydroxy-11α,15(S)-bis-(2-tetrahydropyranyloxy)-15(S)-cyclopentyl-ω-pentanor-prosta-trans-2,trans-13-dienoic acid (prepared as described in Example 43) were dissolved in 10 ml. of diethyl ether and cooled to 0° to −5° C. Then a chromic acid solution (prepared from 1.62 g. of manganese sulphate, 340 mg.

of chromium trioxide, 0.38 ml. of sulphuric acid and 8.0 ml. of water) was added to the solution and the reaction mixture was stirred vigorously at 0° C. for 5 hours and separated into two layers. The aqueous layer was extracted with diethyl ether. The combined organic layer was washed with water and an aqueous sodium chloride solution, dried over magnesium sulphate and concentrated under reduced pressure to give 549 mg. of the title compound having the following physical characteristic:-

TLC (developing solvent methylene chloride:methanol = 19:1), Rf = 0.40.

EXAMPLE 45

9-Oxo-11α,15(S)-dihydroxy-15(S)-cyclopentyl-ω-pentanor-prosta-trans-2,trans-13-dienoic acid [15(S)-Cyclopentyl-ω-pentanor-trans-$\Delta^2$-PGE$_1$]

549 mg. of 9-oxo-11α,15(S)-bis-(2-tetrahydropyranyloxy)-15(S)-cyclopentyl-ω-pentanor-prosta-trans-2,trans-13-dienoic acid (prepared as described in Example 44) were dissolved in a mixture of 6.4 ml. of acetic acid, 2.75 ml. of water and 7 ml. of tetrahydrofuran and stirred at 45° to 50° C. for 6.5 hours. The reaction mixture was then poured into ice-water and extracted with ethyl acetate. The extracts were washed with water and an aqueous sodium chloride solution, dried over magnesium sulphate and concentrated under reduced pressure. The residue was purified by column chromatography on silica gel using a mixture of cyclohexane and ethyl acetate (2:1) as eluent to give 103 mg. of the title compound having the following physical characteristics:

IR (liquid film); $\nu$: 3350, 2930, 1740, 1690, 1645, 970 cm$^{-1}$;

NMR (CDCl$_3$ solution); δ: 7.25 – 6.80 (1H, q), 600 – 5.30 (3H, m), 5.05 – 4.30 (3H, m), 4.20 – 3.70 (2H, m);

TLC (developing solvent chloroform:tetrahydrofuran: acetic acid = 10:2:1); Rf = 0.25.

The present invention includes within its scope pharmaceutical compositions which comprise at least one prostaglandin analogue of general formula VII or a cyclodextrin clathrate thereof or, when R$^2$ represents a hydrogen atom, a non-toxic salt thereof, or an alcohol derivative of a prostaglandin analogue of general formula VII or a cyclodextrin clathrate of such a prostaglandin alcohol, together with a pharmaceutical carrier or coating. In clinical practice such novel compounds will normally be adminstered orally, rectally, vaginally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral adminiatration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.0001% by weight of active substance when required for administration by injection; for oral administration the preparations will normally contain at least 0.001% by weight of active substance. The dose employed depends upon the desired therapeutic effect, the route of administration and the duration of the treatment.

Prostaglandin compounds according to the present invention may be administered orally as bronchodilators by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. Advantageously, the solution to be nebulized is diluted, and aqueous solutions containing from 0.001 to 5 mg., and more particularly 10 to 500 μg, of active ingredient per ml. of solution are particularly suitable. The solution may contain stabilizing agents such as sodium bisulphite and buffering agents to give it an isotonic character, e.g. sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active ingredients in pharmaceutically-acceptable solvents, e.g. ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically-acceptable volatile liquid propellants, in conventional pressurized packs which may be made of any suitable material, e.g. metal, plastics or glass, adequate to withstand the pressures generated by the volatile propellant in the pack. Pressurized pharmaceutically-acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one to two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 and 65 pounds, and more especially between about 30 and 55 pounds, per square inch gauge at 21° C. As is well known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21° C.) and dichlorotetrafluoroethane (vapour pressure 28 pounds per square inch gauge at 21° C.) may be mixed in varying proportions to give propellants having vapour pressures intermediate between those of two constituents, e.g. a mixture of dichlorodifluoromethane and dichlorotetrafluoroethane in the proportions 38:62 respectively by weight has a vapour pressure of 53 pounds per square inch gauge at 21° C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 0.001 to 5 mg., and more particularly 10 to 500 $\mu$g., of active ingredient per ml. of solution or suspension. It is important that the pH of solutions and suspensions used, according to the present invention, to generate aerosols should be kept within the range 3 to 8 and preferable that they should be stored at or below 4° C., to avoid pharmacological deactivation of the active ingredient.

In carrying out the present invention, the means of producing an aerosol for inhalation should be selected in accordance with the physico-chemical properties of the active ingredient.

By the term "pharmaceutically-acceptable" as applied in this specification to solvent, suspending or dispersing agents, propellants and gases is meant solvents, suspending or dispersing agents, propellants and gases which are non-toxic when used in aerosols suitable for inhalation therapy.

In the adult, the daily doses of the prostaglandin analogues of the present invention are generally between 0.1 and 100 $\mu$g./kg. body weight by oral administration in the treatment of hypertension and disorders of the peripheral circulation, between 0.01 and 0.1 ng./kg. body weight per minute by intra-arterial infusion in the prevention and treatment of cerebral thrombosis and myocardial infarction, between 0.5 and 100 $\mu$g./kg. body weight by oral administration in the treatment or gastric ulceration, between 100 $\mu$g. and 5 mg. per person and between 0.1 and 2 $\mu$g. per person by aerosol and intravenous administration, respectively, in the treatment of asthma, and between 10 $\mu$g. and 5 mg./kg. body weight by oral, intravaginal, intravenous and extraamniotic administration for contraception, menstrual regulation, abortion and the induction of labour in female mammals.

The following Examples illustrate pharmaceutical compositions according to the present invention.

EXAMPLE 46

15(S)-Cyclopentyl-$\omega$-pentanor-trans-$\Delta^2$-PGE$_1$ (500 $\mu$g.) was dissolved in ethanol (1 ml.) and the solution obtained was added to an aqueous solution (12 ml.) containing sodium carbonate (50 mg.). Aqueous sodium chloride solution (0.9 w/v, 2 ml.) was then added to give a final volume of 15 ml. The solution was then sterilized by passage through a bacteria-retaining filter and placed in 1.5 ml. portions in 5 ml. ampoules, to give 50 $\mu$g. of 15(S)-cyclopentyl-$\omega$-pentanor-trans-$\Delta^2$-PGE$_1$ (in the form of its sodium salt) per ampoule. The contents of the ampoules were freeze-dried and the ampoules sealed. The contents of an ampoule in a suitable volume, e.g. 3 ml., of physiological saline gave a solution ready for administration by intra-arterial infusion.

EXAMPLE 47

15(S)-Cyclopentyl-$\omega$-pentanor-trans-$\Delta^2$-PGE$_1$ (10 mg.) was dissolved in ethanol (10 ml.), mixed with mannitol (18.5 g.), sieved through a 30-mesh sieve, dried at 30° C. for 90 minutes and again sieved through a 30-mesh sieve. Aerosil (microfine silica; 200 mg.) was added and the powder obtained was machine-filled into one hundred No. 2 hard gelatin capsules to give capsules each containing 100 $\mu$g. of 15(S)-cyclopentyl-$\omega$-pentanor-trans-$\Delta^2$-PGE$_1$, which after swallowing of the capsule is released into the stomach.

What we claim is:

1. A compound of the formula:

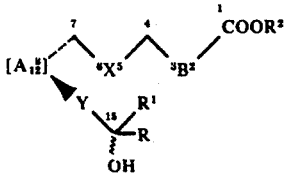

wherein A represents a grouping of the formula:

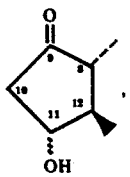

X represents ethylene, Y represents trans-vinylene, B represents trans-vinylene, R represents a hydrogen atom or a straight- or branched-chain alkyl group containing from 1 to 4 carbon atoms, $R_1$ represents cyclo- alkyl of 4–7 carbon atoms, and $R_2$ represents a hydrogen atom or a straight- or branched-chain alkyl group containing from 1 to 12 carbon atoms and cyclodextrin clathrates of such acids and esters and, when $R_2$ represents a hydrogn atom, non-toxic salts thereof.

2. A compound according to claim 1 wherein B represents trans-vinylene and R represents a hydrogen atom.

3. A compound according to claim 1 wherein R represents a hydrogen atom or a methyl group.

4. A compound according to claim 1 wherein $R_1$ represents a cyclobutyl, cyclopentyl or cyclohexyl group.

5. A compound according to claim 1 wherein the hydroxy groups attached to the carbon atom in the 15-position or the 11-position of formulae depicted in claim 1 are in the $\alpha$-configuration.

6. A compound according to claim 1 which is 15(S)-cyclohexyl-$\omega$-pentanor-trans-$\Delta^2$-$PGE_1$.

7. A compound according to claim 1 which is 15(S)-cyclopentyl-$\omega$-pentanor-trans-$\Delta^2$-$PGE_1$.